United States Patent
Bucciarelli et al.

(10) Patent No.: US 7,851,219 B2
(45) Date of Patent: *Dec. 14, 2010

(54) METHODS AND COMPOSITIONS FOR INCREASING PROTEIN YIELD FROM A CELL CULTURE

(75) Inventors: Todd Bucciarelli, Hinsdale, IL (US); Victor Levenson, Oak Park, IL (US); Thomas Primiano, Chicago, IL (US)

(73) Assignee: CDI Bioscience, Madison, WI (US)

( * ) Notice: Subject to any disclaimer, the term of this patent is extended or adjusted under 35 U.S.C. 154(b) by 15 days.

This patent is subject to a terminal disclaimer.

(21) Appl. No.: 12/136,317

(22) Filed: Jun. 10, 2008

(65) Prior Publication Data
US 2009/0142828 A1    Jun. 4, 2009

Related U.S. Application Data

(62) Division of application No. 10/646,129, filed on Aug. 22, 2003, now Pat. No. 7,384,776, which is a division of application No. 09/935,194, filed on Aug. 21, 2001, now Pat. No. 6,635,448.

(60) Provisional application No. 60/226,290, filed on Aug. 21, 2000.

(51) Int. Cl.
*C12N 15/63* (2006.01)
*C12N 1/20* (2006.01)
*C12N 15/00* (2006.01)

(52) U.S. Cl. .................. 435/455; 435/252.3; 435/320.1

(58) Field of Classification Search ........................ None
See application file for complete search history.

(56) References Cited

U.S. PATENT DOCUMENTS

| | | | |
|---|---|---|---|
| 5,888,981 | A | 3/1999 | Bujard et al. |
| 5,891,718 | A | 4/1999 | Hobart et al. |
| 6,274,341 | B1 | 8/2001 | Bailey et al. |
| 6,635,448 | B2 | 10/2003 | Bucciarelli et al. |
| 2002/0160450 | A1 | 10/2002 | Bucciarelli et al. |

FOREIGN PATENT DOCUMENTS

WO    WO 94/04672    3/1994

OTHER PUBLICATIONS

Akiyama, et al., "$G_1$ Phase Accumulation Induced by UCN-01 Is Associated with Dephosphorylation of Rb and CDK2 Proteins as well as Induction of CDK Inhibitor p21/Cip1/WAF1/Sdi1 in p53-mutated Human Epidermoid Carcinoma A431 Cells", *Cancer Research*, vol. 57, pp. 1495-1501, (1997).
Brenner, et al., "Increased *p16* expression with first senescence arrest in human mammary epithelial cells and extended growth capacity with *p16* inactivation", *Oncogene*, vol. 17, pp. 199-205, (1998).
Buchkovich, et al., "The Retinoblastoma Protein Is Phosphorylated during Specific Phases of the Cell Cycle", *Cell*, vol. 58, pp. 1097-1105, (1989).
Burns, et al., "Vesicular stomatitis virus G glycoprotein pseudotyped retroviral vectors: Concentration to very high titer and efficient gene transfer into mammalian and nonmammalian cells", *Proc. Natl. Acad. Sci. USA*, vol. 90, pp. 8033-8037, (1993).
Carlson, et al. "Flavopiridol Induces $G_1$ Arrest with Inhibition of Cyclin-dependent Kinase (CDK) 2 and CDK4 in Human Breast Carcinoma Cells", *Cancer Research*, vol. 56, pp. 2973-2978, (1996).
Campisi, "Cancer, Aging and Cellular Senescence", in Vivo, vol. 14, pp. 183-188, (2000).
Chang, et al., "A Senescence-like Phenotype Distinguishes Tumor Cells That Undergo Terminal Proliferation Arrest after Exposure to Anticancer Agents[1]", *Cancer Research*, vol. 59, pp. 3761-3767, (1999).
Chang, et al., "Effects of $p21^{Waf1/Cip1/Sdi1}$ on cellular gene expression: Implications for carcinogenesis, senescence, and age-related diseases", *PNAS*, vol. 97, No. 8, pp. 4291-4296, (2000).
Chang, et al., "Role of p53 and $p21^{waf1/cip1}$ in senescence-like terminal proliferation arrest induced in human tumor cells by chemotherapeutic drugs", *Oncogene*, vol. 18, pp. 4808-4818, (1999).
Chen, et al., "Cyclin-Binding Motifs Are Essential for the Function of $p21^{CIP1}$", *Molecular and Cellular Biology*, vol. 16, No. 9, pp. 4673-4682, (1996).
Coats, et al., "Requirement of $p27^{Kip1}$, for Restriction Point Control of the Fibroblast Cell Cycle", *Science*, vol. 272, pp. 877-880, (1996).
Cristofalo, et al., "Enzyme Activity during the Growth and Aging of Human Cells in Vitro", *Journal of Cellular Physiology*, vol. 69, pp. 263-272, (1967).
Deng, et al., "Mice Lacking $p21^{CIP1/WAF1}$ Undergo Normal Development, but Are Defective in G1 Checkpoint Control", *Cell*, vol. 82, pp. 675-684, (1995).
Dimri et al., "A biomarker that identifies Senescence human cells in culture and in aging skin in vivo", *Proc. Natl. Acad. Sci. USA*, vol. 92, pp. 9363-9367, (1995).
Dimri et al., "Regulation of Senescence Checkpoint Response by the E2F1 Transcription Factor and $p14^{ARF}$ Tumor Suppressor", *Molecular and Cellular Biology*, vol. 20, No. 1, pp. 273-285, (2000).
Driscoll, et al., "Cyclin $D_1$ antisense RNA destabilizes pRb and retards lung cancer cell growth", *Am. J. Physiol. Soc.*, vol. 273, pp. L941-L949, (1997).
El-Deiry, et al., "WAF1, a Potential Mediator of p53 Tumor Suppression", *Cell*, vol. 75, pp. 817-825, (1993).
Emi, et al., "Pseudotype Formation of Murine Leukemia Virus with the G Protein of Vesicular Stomatitis Virus", *Journal of Virology*, vol. 65, No. 3, pp. 1202-1207, (1991).
Ewen et al., "Functional Interactions of Retinoblastoma Protein with Mammalian D-type Cyclins", *Cell*, vol. 73, pp. 487-497, (1993).

(Continued)

*Primary Examiner*—Michail A Belyavskyi
(74) *Attorney, Agent, or Firm*—McDonnell Boehnen Hulbert & Berghoff LLP

(57) ABSTRACT

Disclosed herein are compositions and methods for increasing protein production from a cell culture. By switching the cells from a replicative to a productive state (RP switch), protein biosynthesis is extended. The productive state is a pseudo-senescent state. This pseudo-senescent state can be induced by transforming the cells with a vector expressing a cell cycle inhibitor. Expression of the cell cycle inhibitor within the cell, because it does not cause cell death, allows for cells to be maintained in culture for longer periods. The invention allows for controlled enhanced protein biosynthetic productivity of cell lines for commercial and research purposes.

19 Claims, 3 Drawing Sheets

OTHER PUBLICATIONS

Fabbrizio, et al., "Inhibition of mammalian cell proliferation by genetically selected peptide aptamers that functionally antagonize E2F activity", *Oncogene*, vol. 18, pp. 4357-4363, (1999).

Fang, et al., "p21$^{war1/Cip1/Sdii}$ induces permanent growth arrest with markers of replicative senescence in human tumor cells lacking functional p53", *Oncogene*, vol. 18. pp. 2789-2797. (1999).

Fero, et al., "A Syndrome of Multiorgan Hyperplasia with Features of Gigantism, Tumorigenesis, and Female Sterility in p27$^{Kip1}$-Deficient Mice", *Cell*, vol. 85, pp.733-744, (1996).

Fussenegger, et al., "Genetic optimization of recombinant glycoprotein production by mammalian cells", *Tibtech*, vol. 17, pp. 35-42, (1999).

Geserick, et al., "Enhanced Productivity During Controlled Proliferation of BHK Cells in Continuously Perfused Bioreactors", *Biotechnology and Bioengineering*, vol. 69, No. 3, pp. 266-274, (2000).

Goldstein, et al., "Studies on the Molecular-Genetic Basis of Replicative Senescence in Werner Syndrome and Normal Fibroblasts", *Experimental Gerontology*, vol. 24, pp. 461-468, (1989).

Gray, et al., "Exploiting Chemical Libraries, Structure, and Genomics in the Search for Kinase Inhibitors", *Science*, vol. 281, pp. 533-538, (1998).

Harper, et al., "The p21 Cdk-Interacting Protein Cip1 Is a Potent Inhibitor of G1 Cyclin-Dependent Kinases", *Cell*, vol. 75, pp. 805-816, (1993).

Hartwell, et al., "Genetic Control of the Cell Division Cycle in Yeast", *Science*, vol. 11, pp. 46-51, (1974).

Hengst et al., "Translational Control of p27' Accumulation During the Cell Cycle", *Science*, vol. 271, pp. 1861-1864, (1996).

Hirai, et al., "Novel INK4 Proteins, p19 and p18, Are Specific Inhibitors of the Cyclin D-Dependent Kinases CDK4 and CDK6", *Molecular and Cellular Biology*, vol. 15, No. 5, pp. 2672-2681, (1995).

Kato, et al., "Cyclic Amp-Induced G1 Phase Arrest Mediated by an Inhibitor (p27$^{Kip1}$) of Cyclin-Dependent Kinase 4 Activation", *Cell*, vol. 79, pp. 487-496, (1994).

Koff, et al., "Formation and Activation of a Cyclin E-cdk2 Complex During the $G_1$ Phase of the Human Cell Cycle", *Science*, vol. 257, pp. 1689-1694, (1992).

Levenson, et al., "Internal Ribosomal Entry Site-Containing Retroviral Vectors with Green Fluorescent Protein and Drug Resistance Markers", *Human Gene Therapy*, vol. 9, pp. 1233-1236, (1998).

Lukas, et al., "Retinoblastoma-protein-dependent cell-cycle inhibition by the tumour suppressor p16", *Nature*, vol. 375, pp. 503-506 (1995).

Matsuoka, et al., "p57$^{KIP2}$, a structurally distinct member of the p21CIP$^1$Cdk inhibitor family, is a candidate tumor suppressor gene", *Genes & Development*, vol. 9, pp. 650-662, (1995).

Mazur, et al., "A Novel Autoregulated Proliferation-Controlled Production Process Using Recombinant CHO Cells". *Biotechnology and Bioengineering*, vol. 65, No. 2, pp. 144-150 (1999).

Mazur, et al., "Higher Productivity of Growth-Arrested Chinese Hamster Ovary Cells Expressing the Cyclin-Dependent Kinase Inhibitor p27", *Biotechnol. Prog.*, vol. 14, pp. 705-713, (1998).

Pear, et al., "Production of high-titer helper-free retroviruses by transient transfection", *Proc. Natl. Acad. Sci. USA*, vol. 90, pp. 8392-8396, (1993).

Polyak, et al., "Cloning of p27$^{Kip1}$, a Cyclin-Dependent Kinase Inhibitor and a Potential Mediator of Extracellular Antimitogenic Signals", *Cell*, vol. 78, pp. 59-66, (1994).

Resnitzky et al., "Acceleration of the $G_1$/S Phase Transition by Expression of Cyclins D1 and E with an Inducible System", *Molecular and Cellular Biology*, vol. 14, No. 3, pp. 1669- 1679, (1994).

Rivard, et al., "Abrogation of p27$^{Kip1}$ by cDNA Antisense Suppresses Quiescence ($G_0$ State) in Fibroblasts", *Journal of Biological Chemistry*, vol. 271, No. 31, pp. 18337-18341, (1996).

Saha, et al., "p21$^{CIP1}$ and Cdc25A: Competition between an Inhibitor and an Activator of Cyclin-Dependent Kinases", *Molecular and Cellular Biology*, vol. 17, No. 8, pp. 4338-4345, (1997).

Schnier, et al., "The Kinase Inhibitor Staurosporine Induces $G_1$ Arrest at Two Points: Effect on Retinoblastoma Protein Phosphorylation and Cyclin-dependent Kinase 2 in Normal and Transformed Cells", *Cancer Research*, vol. 54, pp. 5959-5963, (1994).

Schultz, et al., "Paullones, a Series of Cyclin-Dependent Kinase Inhibitors: Synthesis, Evaluation of CDK1/Cyclin B Inhibition, and in Vitro Antitumor Activity", *J. Med. Chem.*, vol. 42, pp. 2909-2919, (1999).

Serrano et al., "A new regulatory motif in cell-cycle control causing specific inhibition of cyclin D/CDK4", *Nature*, vol. 366, pp. 704-707, (1993).

Serrano et al., "Role of the INK4a Locus in Tumor Suppression and Cell Mortality", *Cell*, vol. 85, pp. 27-37, (1996).

Stein, et al., "Differential Roles for Cyclin-Dependent Kinase Inhibitors p21 and p16 in the Mechanisms of Senescence and Differentiation in Human Fibroblasts", *Molecular and Cellular Biology*, vol. 19, No. 3, pp. 2109-2117, (1999).

Taniguchi, et al., "Induction of the p16$^{INK4a}$ senescence gene as a new therapeutic strategy for the treatment of rheumatoid arthritis", *Nature Medicine*, vol. 5, No. 7, pp. 760-767, (1999).

Toyoshima, et al., "p27, a Novel Inhibitor of G1 Cyclin-Cdk Protein Kinase Activity, Is Related to p21", *Cell*, vol. 78, pp. 67-74, (1994).

Uhrbom, et al., Induction of senescence in human malignant glioma cells by p16$^{INK4A}$, *Oncogene*, vol. 15, pp. 505-514, (1997).

Weber et al., "An SV40 "Enhancer Trap" Incorporates Exogenous Enhancers or Generates Enhancers from Its Own Sequences", *Cell*, vol. 36, pp. 983-992, (1984).

Won, et al., "Growth-regulated expression of D-type cyclin genes in human diploid fibroblasts", *Proc. Natl. Acad. Sci. USA*, vol. 89, pp. 9910-9914, (1992).

Xiong, et al., "p21 is a universal inhibitor of cyclin kinases", *Nature*, vol. 366, pp. 701-704 (1993).

Yee, et al., "A general method for the generation of high-titer, pantropic retroviral vectors: Highly efficient infection of primary hepatocytes", *Proc. Natl. Acad. Sci. USA*, vol. 91, pp. 9564-9568, (1994).

Cao, et al., "Bispecific antibody conjugates in therepeutics." *Advanced Drug Delivery Reviews*, vol. 55, pp. 171-197 (2003).

Fåhraeus, et al., "Characterization of the cyclin-dependent kinase inhibitory domain of the INK4 family as a model for a synthetic tumour suppressor molecule", *Oncogene*, vol. 16, pp. 587-596, (1998).

Freyre, et al., "Very high expression of an anti-carcinoembryonic antigen single chain Fv antibody fragment in the yeast *Pichia pastoris*", *Journal of Biotechnology*, vol. 76, pp. 157-163, (2000).

Harris, et al., Increased frequency of both total and specific monoclonal antibody producing hybridomas using a fusion partner that constitutively expresses recombinant.

Holtkamp, et al., "Isolation of a cloned cell line expressing variant H-2Kk using fluorescence-activated cell sorting", *Nature*, vol. 289, pp. 66-68, (1981).

Huston, et al., "Protein engineering of single chain Fv analogs and fusion proteins", *Methods in Enzymology*, vol. 203, pp. 46-88.

Morrison, et al., "Chimeric human antibody molecules: mouse antigen-binding domain with human constant region domains", Proc. Natl. Acad. Sci. USA, vol. 81.

Nyyssonen, et al., "Efficient production of antibody fragments by the filamentous fungus *Trichoderma reesei*", *Biotechnology* (NY), vol. 11, pp. 591-595, (1993).

Ozato, et al. "Monoclonal antibodies to mouse MHC antigens. III. Hybridoma antibodies reacting to antigents of the H-2$^b$ haplotype reveal genetic control of isotype expression", *Journal of Immunology*, vol. 126, pp. 317-321, (1981).

Riechman, et al., "Reshaping human antibody for therapy", *Nature*, vol. 332, pp. 323-327, (1988).

Shulman, et al., "A better cell line for making hybridomas secreting specific anibodies", *Nature*, vol. 276, pp. 269-270, (1978).

Adams, et al., "Generating improved single-chain Fv molecules for tumor targeting," *J. Immunol. Methods*, vol. 231, pp. 249-260 (1999).

Auchincloss, et al., "Two distinct murine differentiation antigens determined by genes linked to the Ly-6 locus," *J. Immunol.*, vol. 127, No. 5, 1839-1843 (1981).

Baldin, et al., "Cyclin D1 is a nuclear protein required for cell cycle progression in $G_1$," *Genes Dev.*, vol. 7, pp. 812-821 (1993).

Bebbington, et al., "High-level expression of a recombinant antibody from myeloma cells using a glutamine synthetase gene as an amplifiable selectable marker," *Biotechnology*, vol. 10, pp. 169-175 (1992).

Bocharov, et al., "Topology of the secondary structure elements of ribosomal protein L7/L12 from *E. coli* in solution," *FEBS Letters*, vol. 379, pp. 291-294 (1996).

Borrebaeck, et al., "Human monoclonal antibodies: The emperor's new clothes?" *Nat. Biotechnol.*, vol. 17, p. 621 (1999).

Boulianne, et al., "Production of functional chimaeric mouse/human antibody," *Nature*, vol. 312, pp. 643-646 (1984).

Carroll, et al., "Alternative $V_k$ gene rearrangements in a murine B cell lymphoma. An explanation for idiotypic heterogeneity," *J. Exp. Med.*, vol. 168, pp. 1607-1620 (1988).

Carroll, et al., "Mouse X human heterohybridomas as fusion partners with human B cell tumors," *J. Immunol. Methods*, vol. 89, pp. 61-72 (1986).

Chamow, et al., "Immunoadhesins: principles and applications," *Trends Biotechnol.*, vol. 14, No. 2, pp. 52-60 (1996).

Chen, et al., "Cyclin-binding motifs are essential for the function of $p21^{CIP1}$," *Mol. Cell. Biol.*, vol. 16, pp. 4673-4682 (1996).

Co, et al., "Humanized antibodies for antiviral therapy," *Proc. Natl. Acad. Sci.*, vol. 88, pp. 2869-2873 (1991).

Dall'Acqua, et al., "Antibody engineering," *Curr. Opin. Struct. Biol.*, vol. 8, pp. 443-450 (1998).

Davis, et al., "Single chain antibody (SCA) encoding genes: one-step construction and expression in eukaryotic cells," *Biotechnology*, vol. 9, pp. 165-169 (1991).

De Haard, et al., "A large non-immunized human Fab fragment phage library that permits rapid isolation and kinetic analysis of high affinity antibodies," *J. Biol. Chem.*, vol. 274, pp. 18218-1830 (1999).

De St.Groth, et al., "Production of monoclonal antibodies: strategy and tactics," *J. Immunol. Methods*, vol. 35, pp. 1-21 (1980).

Dimri, et al., "Altered profile of transcription factor-binding activities in senescent human fibroblasts," *Exp. Cell Res.*, vol. 212, pp. 132-140 (1994).

Eldin, et al., "High-level secretion of two antibody single chain Fv fragments by *Pichia pastoris*," *J. Immunol. Methods*, vol. 201, pp. 67-75 (1997).

Flores-Rozas, et al., "Cdk-interacting protein 1 directly binds with proliferating cell nuclear antigen and inhibits DNA replication catalyzed by the DNA polymerase delta holoenzyme," *Proc. Natl. Acad. Sci.*, vol. 91, pp. 8655-8659 (1994).

Forster, et al., "Expression of foreign genes in mammalian cells using an antibody fusion system," *Mol. Biotechnol.*, vol. 1, pp. 251-263 (1994).

Galfré, et al., "Rat X rat hybrid myelomas and a monoclonal anti-Fd portion of mouse IgG," *Nature*, vol. 277, pp. 131-133 (1979).

Gillies, et al., "A tissue-specific transcription enhancer element is located in the major intron of a rearranged immunoglobulin heavy chain gene," *Cell*, vol. 33, pp. 717-728 (1983).

Glockshuber, et al., "A comparison of strategies to stabilize immunoglobulin $F_v$-fragments," *Biochemistry*, vol. 29, pp. 1362-1367 (1990).

Graham, et al., "Cloning, expression and characterisation of a single-chain antibody fragment to the herbicide paraquat," *J. Chem. Technol. Biotechnol.*, vol. 63, pp. 279-289 (1995).

Green, et al., "Antigen-specific human monoclonal antibodies from mice engineered with human Ig heavy and light chain YACs," *Nature Genetics*, vol. 7, pp. 13-21 (1994).

Harris, et al., "Anti-CD3-induced changes in protein kinase C isozymes expression in human CD4+ and CD8+ T lymphocytes," *J. Clin. Immunol.*, vol. 15, pp. 232-241 (1995).

Harvill, et al., "In vivo properties of an IgG3-IL-2 fusion protein. A general strategy for immune potentiation," *J. Immunol.* vol. 157, pp. 3165-3170 (1996).

Hayflick, et al., "The Limited in Vitro Lifetime of Human Diploid Cell Strains," *Exp. Cell Res.*, vol. 37, pp. 614-636 (1965).

Hayflick, et al., "The serial cultivation of human diploid cell strains," *Exp. Cell Res.*, vol. 25, pp. 585-621 (1961).

Hendricks, et al., "A high-efficiency vector for expression of foreign genes in myeloma cells," *Gene*, vol. 64, pp. 43-51 (1988).

Hirai et al., "Novel INK4 proteins, p19 and p18, are specific inhibitors of the cyclin D-dependent kinases CDK4 and CDK6," *Mol. Cell Biol.*, vol. 15, No. 5, pp. 2672-2681 (1995).

Horwitz et al., "Secretion of functional antibody and Fab fragment from yeast cells," *Proc. Natl. Acad. Sci.*, vol. 85, pp. 8678-8682 (1988).

Hudson et al., "High avidity scFv multimers; diabodies and triabodies," *J. Immunol. Methods*, vol. 231, pp. 177-189 (1999).

Hudson, et al., "Recombinant antibody constructs in cancer therapy," *Curr. Opin. Immunol.*, vol. 11, pp. 548-557 (1999).

Huennekens, et al., "Tumor targeting:activation of prodrugs by enzyme-monoclonal antibody conjugates" *Trends Biotechonl.* vol. 12, pp. 234-239 (1994).

Hunt, et al., "Characterization and expression of the mouse Hsc70 gene," *Biochim. Biophys. Acta.*, vol. 1444, pp. 315-325 (1999).

Kamb, et al., "Role of a cell cycle regulator in hereditary and sporadic cancer," *Cold Spring Harb Symp Quant Biol.*, vol. 59, pp. 39-47 (1994).

Kang, et al., "Genetic integrity of transforming growth factor $\beta$ (TGF-$\beta$) receptors in cervical carcinoma cell lines: loss of growth sensitivity but conserved transcriptional response to TGF-$\beta$" *Int. J. Cancer.* vol. 77, pp. 620-625 (1998).

Kaufmann, et al., "Comparative analysis of two controlled proliferation strategies regarding product quality, influence on tetracycline-regulated gene expression, and productivity," *Biotechnol. Bioeng.*, vol. 72, No. 5, pp. 592-602 (2001).

Kettleborough, et al., "Optimization of primers for cloning libraries of mouse immunoglobulin genes using the polymerase chain reaction," *Eur. J. Immunol.*, vol. 23, p. 206-211, 1993.

Khazaeli, et al., "Human immune response to monoclonal antibodies" *J. Immunoth.*, vol. 15, pp. 42-52 (1994).

Kilmartin, et al., "Rat Monoclonal antitubulin antibodies derived by using a new nonsecreting rat cell line," *J. Cell Biol.* vol. 93, pp. 576-582 (1982).

Köhler, et al., "Immunoglobulin production by lymphocyte hybridomas," *Eur. J. Immunol.*, vol. 8, pp. 82-88 (1978).

Köhler, et al., "Cellular and molecular restrictions of the lymphocyte fusion" *Curr. Top Microbiol. Immunol.*, vol. 81, pp. 143-148 (1978).

Kotula, et al., "Evaluation of foreign gene codon optimization in yeast: expression of a mouse IG kappa chain," Biotechnology, vol. 9, pp. 1386-1389 (1991).

Kreitman, et al., "Responses in refractory hairy cell leukemia to a recombinant immunotoxin," *Blood*, vol. 94, pp. 3340-3348 (1999).

Kretzschmar, et al., "High-level expression in insect cells and purification of secreted monomeric single-chain Fv antibodies," *J. Immunol. Methods*, vol. 195, pp. 93-101 (1996).

Larrick, et al., "Generation of a protective human monoclonal for the treatment of gram-negative sepsis" *Prog. Clin. Biol. Res.*, vol. 272, pp. 383-393 (1988).

Larrick, et al., "Rapid cloning of rearranged immunoglobulin genes from human hybridoma cells using mixed primers and the polymerase chain reaction" *Biochem. Biophys. Res. Commun.*, vol. 160. pp. 1250-1256 (1989).

Levenson, et al., "Internal ribosomal entry site-containing retroviral vectors with green fluorescent protein and drug resistance markers," *Hum. Gene Ther.*, vol. 9, pp. 1233-1236 (1998).

Lunde, et al., "Antibodies engineered with IgD specificity efficiently deliver integrated T-cell epitopes for antigen presentation by B cells," *Nat. Biotechnol.*, vol. 17, pp. 670-675 (1999).

Mateo, et al., "Humanization of a mouse monoclonal antibody that blocks the epidermal growth factor receptor: recovery of antagonistic activity," *Immunotechnology*, vol. 3, pp. 71-81 (1997).

Mayer, et al., "Taking engineered anti-CEA antibodies to the clinic" *J. Immunol. Methods*, vol. 231, pp. 261-273 (1999).

Melani, et al., "Targeting of interleukin 2 to human ovarian carcinoma by fusion with a single-chain Fv of antifolate receptor antibody," *Cancer Res.*, vol. 58, pp. 4146-4154 (1998).

Mendez, et al., "Functional transplant of megabase human immunoglobulin loci recapitulates human antibody response in mice," *Nat. Genet.*, vol. 15, pp. 146-156 (1997).

Morrison, et al., "Transfectomas provide novel chimeric antibodies," *Science*, vol. 229, pp. 1202-1207 (1985).

Mullis, et al., Specific enzymatic amplification of DNA in vitro: the polymerase chain reaction *Cold Spring Harb. Symp. Quant. Biol.*, vol. 51 Pt 1:263-273 (1986).

Neuberger, et al., "Expression and regulation of immunoglobulin heavy chain gene transfected into lymphoid cells" *EMBO J.*, vol. 2, No. 8, pp. 1373-1378 (1983).

Neuberger, et al., "Monoclonal antibodies. Mice perform a human repertoire," *Nature*, vol. 386, pp. 25-26 (1997).

Neuberger, et al., "Recombinant antibodies possessing novel effector functions" *Nature*, vol. 312, pp. 604-608 (1984).

Noda, et al., "Cloning of senescent cell-derived inhibitors of DNA synthesis using an expression screen," *Exp. Cell. Res.*, vol. 211, pp. 90-98 (1994).

Oi, et al., "Immunoglobulin gene expression in transformed lymphoid cells" *Proc. Natl. Acad. Sci.*, vol. 80, pp. 825-829 (1983).

Orlandi, et al., "Cloning immunoglobulin variable domains for expression by the polymerase chain reaction" *Proc. Natl. Acad. Sci. USA*, vol. 86, pp. 3833-3837 (1989).

Pastan, et al., "Immunotoxins for targeted cancer therapy" Adv. Drug. Deliv. Rev. vol. 31, pp. 53-88 (1998).

Pear, et al., "Production of high-titer helper-free retroviruses by transient transfection" *Proc. Natl. Acad. Sci. USA*, vol. 90, pp. 8392-8396 (1993).

Penichet, et al., "An antibody-avidin fusion protein specific for the transferrin receptor serves as a delivery vehicle for effective brain targeting: initial applications in anti-HIV antisense drug delivery to the brain," *J. Immunol.*, vol. 163, pp. 4421-4426 (1999).

Quelle, et al., "Cloning and characterization of murine p16$^{INK4a}$ and p15$^{INK4b}$ genes," *Oncogene*, vol. 11, pp. 635-645 (1995).

Quelle, et al., "Overexpression of mouse D-type cyclins accelerates G1 phase in rodent fibroblasts," *Genes Dev.*, vol. 7, pp. 1559-1571 (1993).

Rebello, et al., "Anti-globulin responses to rat and humanized CAMPATH-1 monoclonal antibody used to treat transplant rejection," Transplantation, vol. 68, pp. 1417-1420 (1999).

Reff, et al., "High-level production of recombinant immunoglobulins in mammalian cells," *Curr. Opin. Biotechnol.*, vol. 4, pp. 573-576 (1993).

Ridder, et al., "Generation of rabbit monoclonal antibody fragments from a combinatorial phage display library and their production in the yeast *Pichia pastoris*," Biotechnology, vol. 13, pp. 255-260 (1995).

Riechmann, et al., "Expression of an antibody Fv fragment in myeloma cells," *J. Mol. Biol.*, vol. 203, pp. 825-828 (1988).

Riechmann, et al., "Single domain antibodies: comparison of camel VH and camelised human VH domains," *J. Immunol. Methods*, vol. 231, pp. 25-38 (1999).

Romanos, et al., "Foreign gene expression in yeast: a review," *Yeast*, vol. 8, pp. 423-488 (1992).

Saha, et al., "p21$^{CIP1}$ and Cdc25A: competition between an inhibitor and an activator of cyclin-dependent kinases," *Mol. Cell Biol.*, vol. 17, No. 8, pp. 4338-4345 (1997).

Sensel, et al., "Engineering novel antibody molecules," Chem. Immunol. 65:129-58 (1997).

Sharon, et al., "Expression of a $V_H C_k$ chimaeric protein in mouse myeloma cells," *Nature*, vol. 309, pp. 364-367 (1984).

Sheaff, et al., "Tumor suppression. Lessons in p16 from phylum Falconium," *Curr. Biol.*, vol. 5, pp. 28-31 (1995).

Sherr, et al., "Inhibitors of mammalian $G_1$ cyclin-dependent kinases", *Genes & Development*, vol. 9, pp. 1149-1163 (1995).

Smith, et al., "Replicative senescence: Implications for in vivo aging and tumor suppression," *Science*, vol. 273, pp. 63-67 (1996).

Tsao, et al., "Adenovirus-Mediated p21 $^{(WAF1/SDI1/CIP1)}$ gene transfer induces apoptosis of human cervical cancer cell lines," *J. Viral.*, vol. 73, pp. 4983-4990 (1999).

Uhrbom, et al., "Induction of senescence in human malignant glioma cells by p16$^{INK4A}$," *Oncogene*, vol. 15, pp. 505-514 (1997).

Verhoeyen, et al., "Reshaping human antibodies: grafting an antilysozyme activity," *Science*, vol. 239, pp. 1534-1536 (1988).

Vlach, et al., "Growth arrest by the cyclin-dependent kinase inhibitor p$^{27Kip1}$ is abrogated by c-Myc," *Embo. J.*, vol. 15, pp. 6595-6604 (1996).

Waga, et al., "The p21 inhibitor of cyclin-dependent kinases controls DNA replication by interaction with PCNA," *Nature*, vol. 369, pp. 574-578 (1994).

Wileman, et al. "Regulation of plasminogen activation by TGF-β in cultured human retinal endothelial cells," *Br. J. Ophthalmol.*, vol. 84, pp. 417-422 (2000).

Wood, et al., "The synthesis and in vivo assembly of functional antibodies in yeast," *Nature*, vol. 314, pp. 446-449 (1985).

Woodle, et al., "Phase I trial of a humanized, Fc receptor nonbinding OKT3 antibody, huOKT3$_{γ1}$(Ala-Ala) in the treatment of acute renal allograft rejection," *Transplantation*, vol. 68, pp. 608-616 (1999).

Xiong, et al., "Engineering vaccines with heterologous B and T cell epitopes using immunoglobulin genes," *Nat. Biotechnol.*, vol. 15, pp. 882-886 (1997).

Yang, et al., "Eradication of established tumors by a fully human monoclonal antibody to the epidermal growth factor receptor without concomitant chemotherapy," *Cancer Res.*, vol. 59, pp. 1236-1243 (1999).

SEQUENCE LISTING

<160> NUMBER OF SEQ ID NOS: 15

<210> SEQ ID NO 1
<211> LENGTH: 7086
<212> TYPE: DNA
<213> ORGANISM: Artificial Sequence
<220> FEATURE:
<223> OTHER INFORMATION: Description of Artificial Sequence: Expression Vector

<400> SEQUENCE: 1

```
gaattcatac cagatcaccg aaaactgtcc tccaaatgtg tccccctcac actcccaaat      60
tcgcgggctt ctgcctctta gaccactcta ccctattccc cacactcacc ggagccaaag     120
ccgcggccct tccgtttctt tgcttttgaa agacccacc cgtaggtggc aagctagctt     180
aagtaacgcc actttgcaag gcatggaaaa atacataact gagaatagaa aagttcagat     240
caaggtcagg aacaaagaaa cagctgaata ccaaacagga tatctgtggt aagcggttcc     300
tgccccggct cagggccaag aacagatgag acagctgagt gatgggccaa acaggatatc     360
tgtggtaagc agttcctgcc ccggctcggg gccaagaaca gatggtcccc agatgcggtc     420
cagccctcag cagtttctag tgaatcatca gatgtttcca gggtgcccca aggacctgaa     480
aatgaccctg taccttattt gaactaacca atcagttcgc ttctcgcttc tgttcgcgcg     540
cttccgctct ccgagctcaa taaagagcc cacaacccct cactcggcgc gccagtcttc     600
cgatagactg cgtcgcccgg gtacccgtat tcccaataaa gcctcttgct gtttgcatcc     660
gaatcgtggt ctcgctgttc cttgggaggg tctcctctga gtgattgact acccacgacg     720
ggggtctttc atttggggc tcgtccggga tttggagacc cctgcccagg gaccaccgac     780
ccaccaccgg gaggtaagct ggccagcaac ttatctgtgt ctgtccgatt gtctagtgtc     840
tatgtttgat gttatgcgcc tgcgtctgta ctagttagct aactagctct gtatctggcg     900
gacccgtggt ggaactgacg agttctgaac acccggccgc aaccctggga gacgtcccag     960
ggactttggg ggccgttttt gtggcccgac ctgaggaagg gagtcgatgt ggaatccgac    1020
cccgtcagga tatgtggttc tggtaggaga cgagaaccta aaacagttcc cgcctccgtc    1080 tgaattttg cttcggttt ggaaccgaag ccgcgcgtct tgtctgctgc agcgctgcag    1140
catcgttctg tgttgtctct gtctgactgt gtttctgtat ttgtctgaaa attagggcca    1200
gactgttacc actcccttaa gtttgacctt aggtcactgg aaagatgtcg agcggatcgc    1260
tcacaaccag tcggtagatg tcaagaagag acgttgggtt accttctgct ctgcagaatg    1320
gccaaccttt aacgtcggat ggccgcgaga cggcacctt aaccgagacc tcatcaccca    1380
ggttaagatc aaggtctttt cacctggccc gcatggacac ccagaccagg tcccctacat    1440
cgtgacctgg gaagccttgg cttttgaccc ccctccctgg gtcaagccct ttgtacaccc    1500
taagcctccg cctcctcttc ctccatccgc ccgtctctcc cccttgaac ctcctcgttc    1560 gacccgcct cgatcctccc tttatccagc cctcactcct tctctaggcg ccggaattcc    1620
gatctgatca agagacagga tgaggatcgt ttcgcatgat tgaacaagat ggattgcacg    1680
```

```
caggttctcc ggccgcttgg gtggagaggc tattcggcta tgactgggca caacagacaa    1740
tcggctgctc tgatgccgcc gtgttccggc tgtcagcgca ggggcgcccg gttcttttg     1800
tcaagaccga cctgtccggt gccctgaatg aactgcagga cgaggcagcg cggctatcgt    1860
ggctggccac gacgggcgtt ccttgcgcag ctgtgctcga cgttgtcact gaagcgggaa    1920
gggactggct gctattgggc gaagtgccgg ggcaggatct cctgtcatct caccttgctc    1980
ctgccgagaa agtatccatc atggctgatg caatgcggcg gctgcatacg cttgatccgg    2040
ctacctgccc attcgaccac caagcgaaac atcgcatcga gcgagcacgt actcggatgg    2100
aagccggtct tgtcgatcag gatgatctgg acgaagagca tcaggggctc gcgccagccg    2160
aactgttcgc caggctcaag gcgcgcatgc ccgacggcga ggatctcgtc gtgacccatg    2220
gcgatgcctg cttgccgaat atcatggtgg aaaatggccg cttttctgga ttcatcgact    2280
gtggccggct gggtgtggcg gaccgctatc aggacatagc gttggctacc cgtgatattg    2340
ctgaagagct tggcggcgaa tgggctgacc gcttcctcgt gctttacggt atcgccgctc    2400
ccgattcgca gcgcatcgcc ttctatcgcc ttcttgacga gttcttctga gcggactct     2460
ggggttcgaa atgaccgacc aagcgacgcc caacctgcca tcacgagatt cgattccac    2520
cgccgccttc tatgaaaggt tgggcttcgg aatcgttttc cgggacgccg gctggatgat    2580
cctccagcgc gggatctca tgctggagtt cttcgcccac cccgggctcg atcccctcgc    2640
gagttggttc agctgctgcc tgaggctgga cgacctcgcg gagttctacc ggcagtgcaa    2700
atccgtcggc atccaggaaa ccagcagcgg ctatccgcgc atccatgccc ccgaactgca    2760
ggagtgggga ggcacgatgg ccgctttggt cgaggcggat ctgctggttc tttccgcctc    2820
agaagccata gagcccaccg catcccccagc atgcctgcta ttgtcttccc aatcctcccc    2880
cttgctgtcc tgccccaccc cacccccccag aatagaatga cacctactca gacaatgcga    2940
tgcaatttcc tcattttatt aggaaaggac agtgggagtg gcaccttcca gggtcaagga    3000
aggcacgggg gaggggcaaa caacagatgg ctggcaacta aaggcacag tcgaggctga     3060
tcagcgagct ctagcattta ggtgacacta tagaataggg ccctctagat gcataagctt    3120
agatctcgag cggccgcacc ggtccggatc cgagctcggt accaagctta agtttcctct    3180
ctatcactga tagggaaatc tctatcactg atagggagtc ttatatatct actagctccg    3240
gatcactatc actgataggg aaatctctat cactgatagg gactagcatc gatagacctc    3300
ccaccgtaca cgcctaccgc ccatttgcgt caatggggcg gagttgttac gcatttggg     3360
aaagtcccgt tgattttggt gccaaaacaa actcccattg acgtcaatgg ggtggagact    3420
tggaaatccc cgtgagtcaa accgctatcc acgccattg atgtactgcc aaaaccgcat     3480
caccatggta atagcgatga ctaatacgta gatgtactgc caagtaggaa agtcccataa    3540
ggtcatgtac tgggcataat gccaggcggg ccatttaccg tcattgacgt caataggggg    3600
cgtacttggc atatgataca cttgatgtac tgccaagtgg gcagtttacc gtaaatagtc    3660
cacccattga cgtcaatgga aagtcccatt ggcgttact atgggaacat acgtcattat    3720
tgacgtcaat gggcggggt cgttgggcgg tcagccaggc gggccattta ccgtaagtta    3780
tgtaacgcgg aactccatat atgggctatg aactaatgac cccgtaattg attactatta    3840
ataactagtc aataatcaat gtcaacgcgt atatctggcc cgtacatcgc gaagcagcgc    3900
aaaacgccta accctaagca gattcttcat gcaattgtcg gtcaagcctt gccttgttgt    3960
agcttaaatt ttgctcgcgc actactcagc gacctccaac acacaagcag ggagcagata    4020
```

```
ctggcttaac tatgcggcat cagagcagat tgtactgaga gtcgaccata ggggatcggg    4080
agatccggcg ataaaataaa agattttatt tagtctccag aaaaaggggg gaatgaaaga    4140
ccccacctgt aggtttggca agctagctta agtaacgcca ttttgcaagg catggaaaaa    4200
tacataactg agaatagaga agttcagatc aaggtcagga acagatggaa cagctgaata    4260
tgggccaaac aggatatctg tggtaagcag ttcctgcccc ggctcagggc caagaacaga    4320
tggaacagct gaatatgggc caaacaggat atctgtggta agcagttcct gccccggctc    4380
agggccaaga acagatggtc cccagatgcg gtccagccct cagcagtttc tagagaacca    4440
tcagatgttt ccagggtgcc ccaaggacct gaaatgaccc tgtgccttat ttgaactaac    4500
caatcagttc gcttctcgct tctgttcgcg cgcttctgct ccccgagctc aataaaagag    4560
cccacaaccc ctcactcggg gcgccagtcc tccgattgac tgagtcgccc gggtacccgt    4620
gtatccaata aaccctcttg cagttgcatc cgacttgtgg tctcgctgtt ccttgggagg    4680
gtctcctctg agtgattgac tacccgtcag cgggggtctt tcatttgggg gctcgtccgg    4740
gatcgggaga cccctgccca gggaccaccg acccaccacc gggaggtaag ctggctgcct    4800
cgcgcgtttc ggtgatgacg gtgaaaacct ctgacacatg cagctcccgg agacggtcac    4860
agcttgtctg taagcggatg ccgggagcag acaagcccgt cagggcgcgt cagcgggtgt    4920
tggcgggtgt cggggcgcag ccatgaccca gtcacgtagc gatagcggag tgtatactgg    4980
cttaactatg cggcatcaga gcagattgta ctgagagtgc accatatgcg gtgtgaaata    5040
ccgcacagat gcgtaaggag aaaataccgc atcaggcgct cttccgcttc ctcgctcact    5100
gactcgctgc gctcggtcgt tcggctgcgg cgagcggtat cagctcactc aaaggcggta    5160
atacggttat ccacagaatc aggggataac gcaggaaaga acatgtgagc aaaaggccag    5220
caaaaggcca ggaaccgtaa aaaggccgcg ttgctggcgt ttttccatag gctccgcccc    5280
cctgacgagc atcacaaaaa tcgacgctca agtcagaggt ggcgaaaccc gacaggacta    5340
taaagatacc aggcgtttcc ccctggaagc tccctcgtgc gctctcctgt tccgaccctg    5400
ccgcttaccg gatacctgtc cgcctttctc ccttcgggaa gcgtggcgct ttctcatagc    5460
tcacgctgta ggtatctcag ttcggtgtag gtcgttcgct ccaagctggg ctgtgtgcac    5520
gaaccccccg ttcagcccga ccgctgcgcc ttatccggta actatcgtct tgagtccaac    5580
ccggtaagac acgacttatc gccactggca gcagccactg gtaacaggat tagcagagcg    5640
aggtatgtag gcggtgctac agagttcttg aagtggtggc ctaactacgg ctacactaga    5700
aggacagtat ttggtatctg cgctctgctg aagccagtta ccttcggaaa aagagttggt    5760
agctcttgat ccggcaaaca aaccaccgct ggtagcggtg gtttttttgt ttgcaagcag    5820
cagattacgc gcagaaaaaa aggatctcaa gaagatcctt tgatctttc tacggggtct    5880 gacgctcagt ggaacgaaaa ctcacgttaa gggattttgg tcatgagatt atcaaaaagg    5940
atcttcacct agatcctttt aaattaaaaa tgaagtttta atcaatcta aagtatatat    6000 gagtaaactt ggtctgacag ttaccaatgc ttaatcagtg aggcacctat ctcagcgatc    6060
tgtctatttc gttcatccat agttgcctga ctccccgtcg tgtagataac tacgatacgg    6120
gagggcttac catctggccc cagtgctgca atgataccgc gagacccacg ctcaccggct    6180
ccagatttat cagcaataaa ccagccagcc ggaagggccg agcgcagaag tggtcctgca    6240
actttatccg cctccatcca gtctattaat tgttgccggg aagctagagt aagtagttcg    6300
ccagttaata gtttgcgcaa cgttgttgcc attgctgcag gcatcgtggt gtcacgctcg    6360
tcgtttggta tggcttcatt cagctccggt tcccaacgat caaggcgagt tacatgatcc    6420
```

-continued

```
cccatgttgt gcaaaaaagc ggttagctcc ttcggtcctc cgatcgttgt cagaagtaag    6480
ttggccgcag tgttatcact catggttatg gcagcactgc ataattctct tactgtcatg    6540
ccatccgtaa gatgcttttc tgtgactggt gagtactcaa ccaagtcatt ctgagaatag    6600
tgtatgcggc gaccgagttg ctcttgcccg gcgtcaacac gggataatac cgcgccacat    6660
agcagaactt taaaagtgct catcattgga aaacgttctt cggggcgaaa actctcaagg    6720
atcttaccgc tgttgagatc cagttcgatg taacccactc gtgcacccaa ctgatcttca    6780
gcatctttta ctttcaccag cgtttctggg tgagcaaaaa caggaaggca aaatgccgca    6840
aaaaagggaa taagggcgac acggaaatgt tgaatactca tactcttcct ttttcaatat    6900
tattgaagca tttatcaggg ttattgtctc atgagcggat acatatttga atgtatttag    6960
aaaaataaac aaataggggt tccgcgcaca tttccccgaa aagtgccacc tgacgtctaa    7020
gaaaccatta ttatcatgac attaacctat aaaaataggc gtatcacgag gccctttcgt    7080
cttcaa                                                                7086
```

<210> SEQ ID NO 2
<211> LENGTH: 23
<212> TYPE: DNA
<213> ORGANISM: Homo sapiens

<400> SEQUENCE: 2
aggatgttat aaagcatgag tca                                              23

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Cy motif of
      E2F1

<400> SEQUENCE: 3

Lys Arg Arg Leu Asp Leu
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Cy motif of
      E2F2

<400> SEQUENCE: 4

Lys Arg Lys Leu Asp Leu
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Cy motif of
      E2F3

<400> SEQUENCE: 5

Lys Arg Arg Leu Glu Leu
 1               5

<210> SEQ ID NO 6

```
<211> LENGTH: 6
<212> TYPE: PRT
<213> ORGANISM: Artificial Sequence
<220> FEATURE:
<223> OTHER INFORMATION: Description of Artificial Sequence: Cy motif
      from P107Rb

<400> SEQUENCE: 6

Lys Arg Arg Leu Phe Gly
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Cy motif of
      p130Rb

<400> SEQUENCE: 7

Lys Arg Arg Leu Phe Val
  1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Cy motif of
      Cdc6

<400> SEQUENCE: 8

Gly Arg Arg Leu Val Phe
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Cy motif of
      Myt1

<400> SEQUENCE: 9

Pro Arg Asn Leu Leu Ser
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Cy motif of
      Cdc25a

<400> SEQUENCE: 10

Arg Arg Arg Leu Leu Phe
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Cy motif of
      p57

<400> SEQUENCE: 11
```

```
Cys Arg Ser Leu Phe Gly
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Cy motif of
      p27

<400> SEQUENCE: 12

Cys Arg Asn Leu Phe Gly
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Cy motif of
      N terminus of p21

<400> SEQUENCE: 13

Asn Cys Arg Arg Leu Phe Gly
  1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Cy motif of
      C terminus of p21

<400> SEQUENCE: 14

Lys Arg Arg Leu Ile Phe
  1               5

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:
      tetracycline operator

<400> SEQUENCE: 15
tccctatcag ggaga                                                  15
```

METHODS AND COMPOSITIONS FOR INCREASING PROTEIN YIELD FROM A CELL CULTURE

RELATED APPLICATIONS

This application is a divisional application of U.S. Ser. No. 10/646,129, filed Aug. 22, 2003, now U.S. Pat. No. 7,384,776, granted Jun. 10, 2008, which is a divisional application of U.S. Ser. No. 09/935,194, filed Aug. 21, 2001, now U.S. Pat. No. 6,635,448, granted Oct. 21, 2003, which claims priority to U.S. Provisional Application Ser. No. 60/226,290, filed Aug. 21, 2000, which is incorporated herein by reference in its entirety.

BACKGROUND OF THE INVENTION

Manufacturing of biopharmaceuticals depends on cell cultures that secrete protein products into surrounding media. Typically, this conditioned media containing the desired product is used for downstream processing, while a new batch of fresh media is supplied to the cells. Naturally, increasing cell density in the bioreactor can make the process more productive. However, the lifespan of super-dense cultures is much shorter than lower density cultures because continuous proliferation can reduce available attachment surfaces until cell layers detach from solid support. At this stage, the bioreactor has to be recycled: washed, sterilized and re-seeded.

Cell growth can lead to increased product yield until a maximum is reached; then the cycle is repeated. During this cycle the period of maximum cell density and maximum bioreactor efficiency can be relatively short. The length of this period is determined to a large extent by the proliferation rate of producer cells. At the beginning of the cycle, when the seeding density is relatively low, it is advantageous to INCREASE proliferation rate to achieve high cell density faster. On the other hand, it would be favorable to REDUCE the rate of proliferation when the maximal density is achieved in order to preserve cell population at its most productive state. Besides increasing the bioreactor cycle at its production peak, reduced rates of proliferation can channel cell energy from proliferation to protein production, further increasing yields.

Current approaches to increasing the useful time of bioreactor cycle concentrate on media adjustments at or close to the peak of production. The most common method is reduction in serum content of the bioreactor media. While effective in preventing further cell division, this approach can interfere with protein synthesis, thus reducing beneficial effects of decreased cell growth.

Recombinant DNA technology has opened new avenues for the production of useful therapeutic proteins, such as hormones, growth factors, and interferons, in commercial quantities. To economically produce therapeutic proteins at commercial scale, while controlling product quality requires three general steps. First, an effective strategy for maximizing recombinant gene expression, next, a sufficient fermentation process, finally, robust protein recovery and purification processes must be instated.

Elaborate methods of vector construction and cell culture methods are required for production of biopharmaceuticals from mammalian cells. Promoters such as immediate early cytomegalovirus promoter (CMV) can mediate very strong interactions with the transcriptional machinery in most mammalian cellular systems (F. Weber, J. de Villiers, W. Schaffner, Cell 36, 983-92 (1984). Based on this attribute, CMV promoter is frequently used in mammalian expression vectors. High concentrations of protein (mg/ml) are generated using these constructs. The limitation in production of these biopharmaceuticals is generally related to the capacity of the cells to synthesize and secrete the protein product.

Developments in bioprocess engineering of mammalian cells have generally relied on manipulation of culture media components to reduce cell proliferation upon achieving a high density of cells. When the bioreactor is initially seeded with protein-producing cells the efficiency of the process is relatively low because of the low cell density. At this stage cell growth in the bioreactor is the major concern; however, when the cell density reaches its maximum, cell growth becomes detrimental to the system, because cells require additional space and nutrients. Decreasing serum in the media is the most common method of blocking cell proliferation, however, in many cases the core effect of these modifications is reduction of energy level, which is detrimental to the protein synthesis and thus to overall production capacity of the bioreactor.

It would be useful to have a technology that could prevent cell proliferation without affecting protein synthesis to result in increased yields of synthesized bioproducts. An additional benefit of such technology would be diversion of energy, otherwise spent on reproduction, to sustain/increase protein synthesis.

SUMMARY OF THE INVENTION

The invention relates to protein synthesis in general, and increased protein synthetic productivity of cells in particular. By switching the cells from a replicative to a productive state (RP switch), protein biosynthesis can be extended. The productive state is a pseudo-senescent state. This pseudo-senescent state can be induced by transforming the cells with a vector expressing a cell cycle inhibitor. Expression of the cell cycle inhibitor within the cell, because it does not cause cell death, allows for cells to be maintained in culture for longer periods (cell numbers within a culture do not increase and overgrow the growth container). The invention allows for controlled enhanced protein biosynthetic productivity of cell lines for commercial and research purposes.

According to one aspect, the invention is a method of increasing yield of a protein from a cell culture, preferably a eukaryotic cell culture, more preferably a mammalian cell culture, by causing a pseudo-senescent state in one or more cells in the cell culture; and collecting a protein fraction from the cell culture.

According to another aspect, the invention is a method of increasing yield of a protein from a eukaryotic cell culture, by contacting the cell culture with an expression vector which comprises an inducible transcription regulation element comprising a tetracycline operator element, and collecting a protein fraction from the cell culture.

According to yet another aspect, the invention is a transcriptional regulatory element which includes a minimal promoter comprising a TATA sequence, two phased tetracycline operators downstream from the TATA sequence, and two phased tetracycline operators upstream of the TATA sequence.

According to still yet another aspect, the invention is an expression vector including a minimal promoter comprising a TATA sequence, two phased tetracycline operators downstream from the TATA sequence, and two phased tetracycline operators upstream of the TATA sequence.

ABBREVIATIONS AND DEFINITIONS

The following abbreviations are used in this disclosure:

CDK, cyclin-dependent kinase;
CKI, cyclin-dependent kinase inhibitors;
CMV, cytomegalovirus;
DNA, deoxyribonucleic acid;
env, the retrovirus gene encoding the envelope proteins in the membrane of the vital particle;
gag, the retrovirus gene encoding the core proteins of the viral particle;
G418, geneticin (GIBCO, Inc);
kb, kilobases of nucleic acid;
LTR, long terminal repeat;
MoMLV (or MuLV), Moloney strain murine leukemia virus;
mRNA, messenger RNA;
neo, neomycin phosphotransferase;
pA, polyadenylation signal;
pol, the retrovirus gene encoding the viral reverse transcriptase;
RNA, ribonucleic acid;
RP, replicative to productive;
PSI, the packaging nucleotide sequence for murine retroviruses;
tTA, Tc-controlled transactivator;
Tet, teracycline;
TetO, tetracycline operon;
TetR, tetracycline repressor;
TFIID, transcription factor IID; and
T-Rex, tetracycline responsive plasmid vector.

"cell cycle" means the biochemical process by which mammalian cells duplicate themselves.

"cyclin-dependent kinase" is a family of enzymes that trigger progression through the cell cycle.

"CDK inhibitors" are proteins produced naturally by cells to block progression through the cell cycle.

"defective", means genetically-deficient in nucleotide sequences required to produce infectious viral particles.

"defective retroviral vector", means a retroviral vector containing an incomplete RNA genome capable of infecting a host cell, but incapable of producing a viral infection (i.e., with progeny virus) in that cell which could subsequently infect another cell.

"doxycyline" is a water-soluble tetracycline analog suitable for mammalian cell cultures.

"ecotropic receptor" is a protein expressed on the membrane of rodent cells that contains the binding site for mouse leukemia viral particles.

"G418" is a water-soluble form of neomycin suitable for mammalian cell cultures.

"packaged", means assembling the recombinant murine retrovirus genome into an infectious retroviral vector by surrounding the recombinant retroviral RNA with the gag and pol proteins to form a core particle and encapsulating the core particle in a membrane containing the env protein.

"packaging cell", means a cell containing a proviral genome of a first defective retroviral vector that encodes viral proteins sufficient to assemble a second defective retroviral vector into an infectious retroviral vector virion.

"promoter" is a region of DNA where transcription is initiated.

"proviral genome", means a defective retroviral vector nucleic acid integrated in the DNA of a host cell.

"pseudo-senescent" cells are cells forced to express a senescent phenotype by manipulation. Pseudo-senescent cells do not include aged cells that have naturally senesced. Cells in a forced or pseudo-senescent state may have prolonged cell culture lifetimes (S. Goldstein, D. P. Singal, *Exp Cell Res* 88, 359-64 (1974); A. J. Brenner, M. R. Stampfer; and C. M. Aldaz, *Oncogene* 17, 199-205 (1998)), are resistant to apoptosis (B. D. Chang, et al., *Proc Natl Acad Sci USA* 97, 4291-6 (2000); and D. Javelaud, J. Wietzerbin, O. Delattre, F. Besancon, *Oncogne* 19, 61-8 (2000) and increase their protein synthetic capacity several fold (B. D. Chang, et al., *Proc Natl Acad Sci USA* 97, 4291-6 (2000); V. J. Cristofalo, D. Kritchevsky, *Prog Immunobiol Stand* 3, 99-105 (1969); and G. H. Stein, L. F. Drullinger, A Soulard, V. Dulic, *Mol Cell Biol* 19, 2109-17 (1999).

"retroviral vector" means a genetically-engineered recombinant retrovirus containing a gene of interest, capable of infecting a mammalian cell wherein the gene of interest can become integrated into the genome of the mammalian cell in a manner that promotes the expression of the gene of interest.

"retrovirus", means an infectious RNA virus having an RNA genome that is converted to DNA and integrated into the genome of the host cell.

"selecting", means cloning (e.g., by limiting dilution), killing undesirable cells (e.g., with drugs or toxins), or mechanical (e.g., by fluorescence activated cell sorting) or physical methods (e.g., by microscopic micropipetting) for collecting individual cells with desirable properties.

"sense orientation" means the direction of DNA sequence in a vector to produce a certain peptide or protein.

"tetracycline" is a naturally occurring antibiotic that is active against bacteria by binding to ribosomes and preventing protein synthesis.

"tetracycline repressor" is a helix-turn-helix protein that forms homodimeric complex that binds tightly to the tetracycline operator.

"tetracycline operator" is a 15 bp palindomic sequence (TCCCTATCAGGGAGA; SEQ ID NO:15) that is bound by tetracycline repressor.

"TFIID" is a core protein necessary for transcription of RNA from DNA at a promoter site.

"transactivator" means a protein that binds to regulatory regions of DNA and enhances the expression of its associated gene.

"transcription" means the process by which the sequence of DNA is used as a template to produce a corresponding piece of RNA.

"vector" means an entity of DNA constructed to introduce and express a set of genes in cells.

"viral particles" is used synonymously with "virions" to mean an infectious virus having a ribonucleoprotein core particle surrounded by a membrane containing envelope protein.

DETAILED DESCRIPTION OF THE INVENTION

Figure 1:
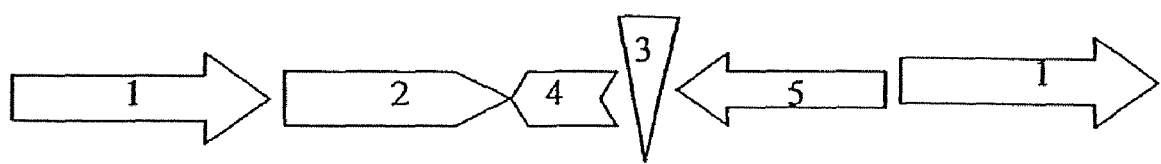
FIG. 1. is a diagram of the regulatory elements of the of the LNtCtX with PolyA vector. The regulatory elements include the viral long terminal repeat (LTR) (1), a selection marker (2), and a multiple cloning site (3) flanked by a polyadenylation signal (4) and a regulated promoter (5).

The present invention provides compositions and methods for producing a pseudo-senescent state in a cell culture for the purpose of increasing protein yield from the culture. By placing the cells in a pseudo-senescent state, the cell density of a culture may be maintained for a longer period without overgrowth of the culture leading to cell death. Essentially, any cell type may be used. Furthermore, the yield of essentially any protein may be improved including secreted proteins, membrane proteins, and intracellular proteins. In preferred embodiments, the protein is secreted by the cells. For example, a hybridoma cell line may be placed in a pseudo-senescent state to increase the yield of monoclonal antibody from a culture of the hybridoma cell culture. In light of the present disclosure, other protein production systems in which the present invention may be applied will become apparent to those of skill in the art.

In preferred embodiments, the invention involves arresting cell division by conditionally expressing known blockers of the cell cycle. The stable introduction of the full-length coding regions of cell cycle inhibitor genes or fragments of such genes under control of inducible promoters not only stop cell division, but also induce differentiation to a senescence-like (pseudo-senescent) state. Senescence can be characterized by an increase in cell volume, a flattened morphology, and increased protein synthesis. Such cells have longer lifespan and are also substantially more resistant to environmental stresses, such as lowered pH, loss of serum factors, osmotic changes and other impedance that triggers cell death in proliferating population. By this virtue, the present invention increases cell stability and allows higher concentration of secreted products. As a result, complex media or repetitive exchange of media can be circumvented.

In certain embodiments, the present invention allows controlled cell growth arrest without adverse effects on protein synthesis, by increasing the controlled expression of factors that arrest the cell cycle. Such arrest provides two important benefits: (1) it lengthens the phase of maximum production phase of bioreactor cycle; (2) it reduces/eliminates energy requirements for proliferation and thus shifts energy into protein production increasing the output. Combination of both effects can increase overall output from one bioreactor cycle at least ten-fold without any changes in the bioreactor design or principles of operation.

In order to produce a pseudo-senescent state in a cell, embodiments of this invention directly manipulate the progress of the cell cycle. The process of cellular reproduction is known as the cell cycle (A. Murray, T. Hunt, *The Cell Cycle: An Introduction* (Freeman Press, New York, ed. 1st, 1993)). Parental cell goes through a series of steps, eventually producing two daughter cells. Continuous proliferation depends on correct duplication of the genome and of the cell mass and equitable separation of chromosomes and cellular material to the daughter cells.

The cell cycle can be divided into four phases:

S (synthetic) phase: the entire genome is duplicated. In this phase cellular energy is used to synthesize enzymes essential for nucleotide synthesis, followed by DNA replication, proofreading the finished product and correcting detected mistakes.

M (mitotic) phase: parental cell needs energy to compact the entire duplicated genome into chromosomes, to produce a complex protein scaffold, the mitotic spindle, to attach, align and pull apart the duplicated chromosomes. This is followed by cytokinesis, when the cell divides, forming two identical cells.

G1 (gap) phase: the period between M and S phases. The longest phase of the cell cycle. Its length depends on the type of cell as well as its environment. If sufficient nutrition or growth stimulus is not available cells will stop in G1 and not enter S phase (A. Murray, T. Hunt, *The Cell Cycle: An Introduction* (Freeman Press, New York, ed. 1st, 1993)). Following exit from M, cells can escape from the cell cycle into a non dividing state; this is usually followed by terminal differentiation.

G2 phase: the period after S phase and before mitosis. Cells generally do not spend much time in this phase, but divide soon after S phase is complete.

Precise coordination of the cell cycle events is required for successful reproduction. Completion of the S phase is essential before the cell passes its genetic material to daughter cells. Any mistake at this stage can be fatal to the progeny, and cells have developed elaborate mechanisms for controlled entry into S and M phases. The paradigm of cell cycle regulation requires orderly execution of cell cycle events, so that the completion of one event is necessary for the beginning of the next (L. Hartwell, K. Mortimer, J. Culotti, M. Culotti, *Genetics* 74, 267 (1973)). Regulatory feedback controls, that keep the cell cycle from progressing if an essential event does not occur, are called checkpoints. Genes, responsible for controlled progression of cell cycle, were first described as cell division cycle (cdc) genes in budding yeast (L. H. Hartwell, J. Culotti, J. R. Pringle, B. J. Reid, *Science* 183, 46-51 (1974)); (L. H. Hartwell, *Bacteriol Rev* 38, 164-98 (1974)). The majority of cdc genes turned out to be either protein kinases or protein phosphatases; one of the most important among them is protein kinase cdc2. Homologues to cdc2, called cyclin-dependent kinases (CDKs) regulate the cell cycle in higher eukaryotes. CDK-mediated transfer of phosphate groups to target proteins facilitates their activation or repression, which ultimately results in the progress of the cell cycle. Activation of CDKs depends on their association with protein co-factors—cyclins (D. J. Lew, V. Dulic, S. I. Reed, *Cell* 66, 1197-206 (1991)).

Each phase of the cell cycle is characterized by a unique pattern of CDK activity (C. J. Sherr, *Cell* 73, 1059-65 (1993); C. J. Sherr, *Cell* 79, 551-5 (1994); and S. van den Heuvel, E. Harlow, *Science* 262, 2050-4 (1993)). Eight CDKs have been identified in mammalian cells, and most are active in certain phases of the cell cycle. Thus, progression through G1 depends on the activities of CDK2, CDK3, CDK4, and CDK6, while CDK2 and cdc2 are active in S phase, and cdc2 governs entry and exit into mitosis.

Likewise, cyclins are a group of related proteins that contain a conserved region of homology (the cyclin box) and are expressed in specific phases of the cell cycle (D. O. Morgan, *Nature* 374, 131-4 (1995)). Cyclin levels are rate limiting for the actions of CDKs.

D-type cyclins and cyclin E are expressed in GI phase of the cycle, when they are involved in regulation of entry into S phase A (Koff, et al., *Cell* 66, 1217-28 (1991); Y. Xiong, H. Zhang, D. Beach, *Cell* 71, 505-14 (1992); and C. J. Sherr, J. Kato, D. E. Quelle, M. Matsuoka, M. F. Roussel, *Cold Spring Harb Symp Quant Biol* 59, 11-9 (1994)). These cyclins associate with CDK4/6 and CDK2, respectively. There are three types of D cyclins (F. Weber, J. de Villiers, W. Schaffner, *Cell* 36, 983-92 (1984); A. Murray, T. Hunt, *The Cell Cycle: An Introduction* (Freeman Press, New York, ed. 1st, 1993); and L. Hartwell, K. Mortimer, J. Culotti, M. Culotti, *Genetics* 74, 267 (1973)), and these are expressed in a cell-type specific fashion (C. J. Sherr, *Cell* 73, 1059-65 (1993); C. J. Sherr, *Cell* 79, 551-5 (1994)). Cyclin D is expressed early in G1 when quiescent (non-dividing) cells are stimulated by environmental or growth factors to enter the cell cycle. Cyclin D levels remain high as long as mitogen levels are elevated. These proteins are labile (half-life of 20 minutes), and their production depends on the continued presence of mitogens (C. J. Sherr, J. Kato, D. E. Quelle, M. Matsuoka, M. F. Roussel,

*Cold Spring Harb Symp Quant Biol* 59, 11-9 (1994)). Hence, growth factor or serum deprivation lowers cyclin D levels and halts the cell cycle in G1. Forcing the expression of cyclin D accelerates progression through G1 (D. E. Quelle, et al., *Genes Dev* 7, 1559-71 (1993); and D. Resnitzky, M. Gossen, H. Bujard, S. I. Reed, *Mol Cell Biol* 14, 1669-79 (1994)) and its inhibition blocks cells in G1 (V. Baldin, J. Lukas, M. J. Marcote, M. Pagano, G. Draetta, *Genes Dev* 7, 812-21 (1993)). Cyclin E activity is also required in G1, although following cyclin D activity (M. Ohtsubo, A. M. Theodoras, J. Schumacher, J. M. Roberts, M. Pagano, *Mol Cell Biol* 15, 2612-24 (1995); J. A. Knoblich, et al., *Cell* 77, 107-20 (1994)). Cyclin E activity peaks at the G1-S boundary, and decays as S phase progresses (M. Ohtsubo, A. M. Theodoras, J. Schumacher, J. M. Roberts, M. Pagano, *Mol Cell Biol* 15, 2612-24 (1995); A. Koff, et al., *Science* 257, 1689-94 (1992); and V. Dulic, E. Lees, S. I. Reed, *Science* 257, 1958-61 (1992)). Cyclin E is regulated transcriptionally by E2F and also by proteolysis, and is required for entry into S phase (D. Resnitzky, M. Gossen, H. Bujard, S. I. Reed, *Mol Cell Biol* 14, 1669-79 (1994); M. Ohtsubo, A. M. Theodoras, J. Schumacher, J. M. Roberts, M. Pagano, *Mol Cell Biol* 15, 2612-24 (1995); J. A. Knoblich, et al., *Cell* 77, 107-20 (1994), and M. Ohtsubo, J. M. Roberts, *Science* 259, 1908-12 (1993)). Later cell cycle transitions are mediated by cyclin A and B. Cyclin A associates with CDK2 and cdc2 and its activity is required in S phase and for the G2-M transition (M. Pagano, R. Pepperkok, F. Verde, W. Ansorge, G. Draetta, *Embo J* 11, 961-71 (1992); A. Giordano, et al., *Cell* 58, 981-90 (1989); and F. Girard, U. Strausfeld, A. Fernandez, N. J. Lamb, *Cell* 67, 1169-79 (1991). Cyclin B associates with cdc2 and regulates mitotic entry and exit. Cyclin-dependent kinases (CDKs) are also regulated by phosphorylation and dephosphorylation (D. O. Morgan, *Nature* 374, 131-4 (1995)). The site of CDK activation is a conserved threonine residue within a T loop (H. L. De Bondt, et al., *Nature* 363, 595-602 (1993)). The binding of cyclin and the phosphorylation of the CDK move the T loop away from the catalytic site of the enzyme allowing substrate to bind. Conversely, phosphorylation of tyrosine in the N-terminal region inhibits CDK activity. Enzymes that inactivate CDKs by adding phosphate to these tyrosine groups are conserved in many species and are known as wee1 and mik1 kinases (R. Heald, M. McLoughlin, F. McKeon, *Cell* 74, 463-74 (1993); M. Igarashi, A. Nagata, S. Jinno, K. Suto, H. Okayama, *Nature* 353, 80-3 (1991); K. Lundgren, et al., *Cell* 64, 1111-22 (1991); and P. Russell, P. Nurse, *Cell* 49, 559-67 (1987)). Dephosphorylation of CDKs is mediated by cdc25 phosphatase. A balance of these activities sets a threshold for CDK activation and determines mitotic entry. Thus, CDKs, through their ability to regulate cyclins, play a central role in controlling cell proliferation.

A critical regulator of cell cycle progression in mammalian cells is the family of Rb proteins. Rb proteins undergo phosphorylation during G1, which modifies its interaction with a critical transcription factor E2F (K. Buchkovich, L. A. Duffy, E. Harlow, *Cell* 58, 1097-105 (1989); S. Mittnacht, et al., *Embo J* 13, 118-27 (1994); and J. R. Nevins, *Science* 258, 424-9 (1992)). E2F transcription factors are heterodimeric DNA binding proteins composed of one E2F factor and one DP factor that are required for the transcriptional regulation of many proteins needed for S phase progression (W. G. Kaelin, Jr., et al., *Cell* 70, 351-64 (1992); K. Helin, et al., *Cell* 70, 337-50 (1992); C. L. Wu, L. R. Zukerberg, C. Ngwu, E. Harlow, J. A. Lees, *Mol Cell Biol* 15, 2536-46 (1995)). There are five known E2F factors, and 3 DP factors. When complexed with Rb, E2F is inactive or may even function as a repressor, thereby silencing E2F-dependent promoters, which, in turn, arrests the cell cycle for a lack of the needed gene products. Phosphorylation of Rb regulates E2F activity. Unphosphorylated Rb avidly binds E2F in early G1, but its phosphorylation at multiple sites lowers its affinity for E2F and releases it to complex with DP in late G1.

The CDKs are responsible for the phosphorylation of Rb. The Rb protein has eight consensus phosphorylation sites and CDKs complexed with cyclin D, E, and A have Rb kinase activities (J. A. Lees, K. J. Buchkovich, D. R. Marshak, C. W. Anderson, E. Harlow, *Embo J* 10, 4279-90 (1991); S. F. Dowdy, et al., *Cell* 73, 499-511 (1993); and M. E. Ewen, et al., *Cell* 73, 487-97 (1993)). Cyclin D-CDK 4 has very high affinity for dephophorylated Rb (J. Kato, H. Matsushime, S. W. Hiebert, M. E. Ewen, C. J. Sherr, *Genes Dev* 7, 331-42 (1993)). Cyclin B-CDK4/6 and cyclin E-CDK2 cooperate to inactivate the E2F binding of Rb. The cyclin D function is not essential in Rb-deficient cell lines, suggesting the function of D-type cyclins of promoting G1 phase progression (S. Bates, et al., *Oncogene* 9, 1633-40 (1994); and J. Lukas, et al., *Nature* 375, 503-6 (1995)). Cyclin E-CDK2 may also be necessary for G1/S phase transition (M. Ohtsubo, A. M. Theodoras, J. Schumacher, J. M. Roberts, M. Pagano, *Mol Cell Biol* 15, 2612-24 (1995)).

Thus, progression of the cell cycle involves many factors within the cell. In light of the present disclosure, one of skill in the art would recognize that one or several of these factors may be utilized or targeted to cause a pseudo-senescent state in a cell. Described below are examples of such.

CDK Inhibitors (CKIs)

An important aspect of the present invention is the inhibition of cell proliferation. Because CDKs play an essential role in cell proliferation, inhibitors of CDK activity are particularly useful in the compositions and methods of the present invention. All organisms express proteins that directly bind to and inhibit CDK activity (C. J. Sherr, J. M. Roberts, *Genes Dev* 9, 1149-63 (1995); and M. Peter, I. Herskowitz, *Cell* 79, 181-4 (1994)). These inhibitors provide another means of cell cycle control in response to diverse stimuli.

Mammalian cells express two classes of CKIs that are distinguished by their CDK targets. The members of the Cip/Kip family of CKIs are universal inhibitors, and INK4 proteins are specific for CDK4/6 inhibition (C. J. Sherr, J. M. Roberts, *Genes Dev* 9, 1149-63 (1995). The Cip/Kip family members are p21, p27, and p57. Over-expression of these gene products blocks cells in G1 phase in culture. They are able to inhibit all cyclin-CDK complexes in vitro. These proteins bind avidly to cyclin-CDK complexes, more so than to the factors separately.

p21 was first identified as a component of cyclin-CDK complexes in proliferating cells and as a protein induced as cells become senescent (Y. Xiong, H. Zhang, D. Beach, *Genes Dev* 7, 1572-83 (1993); and A. Noda, Y. Ning, S. F. Venable, O. M. Pereira-Smith, J. R. Smith, *Exp Cell Res* 211, 90-8 (1994)). p21 has two functional domains, an N-terminal CDK binding region, and a carboxy-terminal region that associates with PCNA, a processing factor for DNA polymerase delta (S. Waga, G. J. Hannon, D. Beach, B. Stillman, *Nature* 369, 574-8 (1994); H. Flores-Rozas, et al., *Proc Natl Acad Sci USA* 91, 8655-9 (1994); and Y. Luo, J. Hurwitz, J. Massague, *Nature* 375, 159-61 (1995)) One role proposed for p21 is to mediate cell cycle arrest.

The CDK inhibitor p27 is structurally related to p21 (K. Polyak, et al., *Cell* 78, 59-66 (1994); and H. Toyoshima, T. Hunter, *Cell* 78, 67-74 (1994)). p21 and p27 share significant N-terminal homology within the CDK inhibitory domain. p27 does not contain a PCNA interaction domain. Unlike p21, p27 is not regulated by p53, p27 levels do respond to a number of mitogenic or anti-mitogenic stimuli (C. J. Sherr, J. M. Roberts, *Genes Dev* 9, 1149-63 (1995)). In general, p27 levels are low in dividing cells, and elevated in growth-arrested cells. The regulation of p27 is complex, involving mechanisms at the transcriptional, translational and posttranslational levels (L. Hengst, S. I. Reed, *Science* 271, 1861-4 (1996)).

The mechanism of p27 inhibition has been clarified by crystal structure of p27 bound to the cyclin A-CDK2 complex (A. A. Russo, P. D. Jeffrey, N. P. Pavletich, *Nat Struct Biol* 3, 696-700 (1996)). Separate domains of p27 interact with cyclin A and CDK2. Dramatic alterations in the structure of CDK2 upon p27 binding implicate a distortion of the ATP binding site resulting in the inhibition of CDK2 kinase activity.

Less is known about p57, which was cloned by its homology to p27 (M. H. Lee, I. Reynisdottir, J. Massague, *Genes Dev* 9, 639-49 (1995); S. Matsuoka, et al., *Genes Dev* 9, 650-62 (1995)). Both amino and carboxy-terminal inhibitory domains are similar to p27, however, its expression is restricted to terminally differentiated tissues.

The INK4 family of CKIs includes four structural proteins (p15, p16, p18, and p19), each of which contains four ankyrin repeats (C. J. Sherr, J. M. Roberts, *Genes Dev* 9, 1149-63 (1995)). The first member of this family to be identified, p16, was found to be associated with CDK4 in transformed cells and subsequently was identified as a tumor suppressor in familial melanoma (M. Serrano, G. J. Hannon, D. Beach, *Nature* 366, 704-7 (1993); R. J. Sheaff, J. M. Roberts, *Curr Biol* 5, 28-31 (1995); and A. Kamb, *Cold Spring Harb Symp Quant Biol* 59, 39-47 (1994)). INK4 proteins bind to monomeric CDK4/6 subunits, preventing their association with D-type cyclins, and INK4 proteins also can inhibit the activity of cyclin D-CDK4/6 complexes.

The INK4 proteins p15, p18, and p19 are expressed ubiquitously in mouse tissues and cultured cells, and the expression of p19 oscillates within the cell cycle (D. E. Quelle, et al., *Oncogene* 11, 635-45 (1995); and H. Hirai, M. F. Roussel, J. Y. Kato, R. A. Ashmun, C. J. Sherr, *Mol Cell Biol* 15, 2672-81 (1995)). Although p15 is involved in the anti-proliferative actions of TGF-β, the physiological roles of INK4 remain unknown. The frequent deletions of p15 and p16 in primary tumors and the high incidence of tumors in p16-deficient mice indicate that these proteins play a critical role in maintaining normal growth control (M. Serrano, et al., *Cell* 85, 27-37 (1996)).

Several independent laboratories have demonstrated successful arrest of asynchronous cell culture in G1 phase of the cell cycle upon introduction (A. Noda, Y. Ning, S. F. Venable, O. M. Pereira-Smith, J. R. Smith, *Exp Cell Res* 211, 90-8 (1994); J. Vlach, S. Hennecke, K. Alevizopoulos, D. Conti, B. Amati, *Embo J* 15, 6595-604 (1996); and T. K. Kwon, A. A. Nordin, *Biochem Biophys Res Commun* 238, 534-8 (1997)) or upon induction (B. B. McConnell, M. Starborg, S. Brookes, G. Peters, *Curr Biol* 8, 351-4 (1998); L. Fang, et al., *Oncogene* 18, 2789-97 (1999); L. Uhrbom, M. Nister, B. Westermark, *Oncogene* 15, 505-14 (1997); and B. D. Chang, et al., *Proc Natl Acad Sci USA* 97, 4291-6 (2000)) of specific inhibitors of cyclin-dependent kinases (CKIs). Accumulated evidence indicate that expression of p16, p27 or p14ARF arrest cells in GI phase of the cell cycle (J. Vlach, S. Hennecke, K. Alevizopoulos, D. Conti, B. Amati, *Embo J* 15, 6595-604 (1996); L. Uhrbom, M. Nister, B. Westermark, *Oncogene* 15, 505-14 (1997); and G. P. Dimri, K. Itahana, M. Acosta, J. Campisi, *Mol Cell Biol* 20, 273-85 (2000)); apparently, in many instances p21 expression will also have the same effect (A. Noda, Y. Ning, S. F. Venable, O. M. Pereira-Smith, J. R. Smith, *Exp Cell Res* 211, 90-8 (1994); and L. Fang, et al., *Oncogene* 18, 2789-97 (1999)), although prolonged expression of this CKI may initiate apoptosis (Y. P. Tsao, et al., *J Virol* 73, 4983-90 (1999)).

In certain embodiments of the present invention, CKI expression may be stimulated within a cell or be the result of expression of a heterologous copy of the CKI introduced into the cell. In preferred embodiments, more than one different heterologous CKI is introduced into the cell. For example, heterologous copies of p16, p21, and p57 or p27 may be introduced into a cell.

When a heterologous copy of a CKI is introduced into a cell, it is preferable that the CKI gene is encoded within an expression vector. Even more preferable is that the expression vector be maintained in the cell during cell division. Thus, a retroviral vector, because it is replicated and maintained within genome of the host cell, is particularly useful. Furthermore, because even low levels of expression of the CKI may prevent cell division, it is preferable that expression of the CKI be tightly regulated. Expression of the CKI is turned off to allow growth of the cells within a culture. When the cells reach a desired concentration, the CKI may be turned on, halting cell growth by the production of a pseudo-senescent state.

Of course, other compounds and compositions may be used to produce a pseudo-senescent state within cells. In addition to CKIs, other genes may be used or targeted, such as, E2F2, E2F4 and the cyclins D1 and D2. Current data indicate that E2F family members can act either as activators or as sequesterors of Rb family members. Since E2F2 most frequently acts as an activator (DeGregori et al., 1997), blocking its expression using inducible antisense constructs achieves cell cycle arrest. E2F4, on the other hand, has been implicated in sequestering pRb/p130 (Fabbrizio et al., 1999; Furukawa et al., 1999), acting as a negative regulator of the cell cycle. Thus, to arrest cells in G1, an inducible sense-oriented construct of E2F4 is used. Apparently, similar relationship exists between cyclins D1 and D2: D1 is an immediate early gene, induced after serum stimulation of resting fibroblasts (Won et al., 1992). To arrest cells in G1 an antisense construct of cyclin D1 is to be used. Cyclin D2, on the other hand, is induced in senescent cells (Meyyappan et al., 1998); it is likely that it counteracts activity of D1, possibly by sequestering some common factors. This gene may be used as a sense-oriented construct to induce pseudo-senescence.

To further increase cell endurance and to optimize the pseudo-senescent phenotype, additional modifications of producer cells may be required; depending on the cell type these may include introduction of wild type p53, E2F4, cyclin D2, JunB, NF-κB, HSP72. When multiple expression vectors are introduced it is preferable to express a different resistance marker in order to facilitate selection of appropriate expressing clones.

Other means of blocking cell cycle progression use small molecules or peptides. The small molecules or peptides may be kinase inhibitors. Examples includes compounds that inhibit the kinase activities of cyclin-CDKs, such as the paullones, which selectively inhibit CDK1/cyclin B (Kunick, 1999; Link et al., 1999; Schultz et al., 1999), butyrolactones, that inhibit CDKs 1, 2 and 5 (Furukawa et al., 1996; Kitagawa et al., 1994; Kitagawa et al., 1993; Suzuki et al., 1999) competitors of the STP-binding domain, such as olomoucine, purvalanol A, and roscovitine (Abraham et al., 1995; De Azevedo et al., 1997; Gray et al., 1998; Meijer et al., 1997). Addition of these compounds in the growth media promotes pseudo-senescence and may be used to further enhance production of proteins.

Other examples include protease inhibitors. CDK inhibitors, such as p21, p27, are normally turned over at very high rates. These proteins have half-lives of about 20 min in cell culture (Baldin et al., 1993; Quelle et al., 1993). Blocking the turnover of CKIs using a proteosome inhibitor, for example MG132 (Hunt et al., 1999), will sustain high levels of CKIs thereby enhancing the cell cycle arrest produced by the RP shift.

Other compound may be used. Flavopiridol blocks CDK activity by interfering with cyclin D binding to CDK2 (Carlson et al., 1996; Patel et al., 1998). However, flavopiridol causes enhanced apoptosis at the concentrations used in these studies (Schwartz et al., 1997). Thus, it is preferred that, if flavopiridol is used, it is used at concentrations that do not cause apoptosis. Likewise, 7-hydroxystaurosporine (UCN01), which was initially developed as a selective protein kinase C inhibitor, has an anti-tumor effect on several human cancer cell lines in vivo (Kawakami et al., 1996). UCN01 inhibits the kinase activity of CDKs and promotes accumulation of dephosphorylated Rb thus halting cells in G1 (Akiyama et al., 1997; Gong et al., 1994; Schnier et al., 1994) This compound also produces apoptosis at higher concentrations (Shao et al., 1997). It is likely that low concentrations of this agent could augment the RP shift.

Peptides that may be used include Cy region peptides. The cyclin binding Cy motif of the CIP/KIP family of CDK inhibitors (Chen et al., 1996) can interact with the cyclins independently of CDK2. The cyclin-binding motifs of p21 are required for the optimal inhibition of cyclin-CDK kinases in vitro and for growth suppression in vivo. Peptides containing only the N-terminal or C-terminal motif of p21 partially inhibit cyclin-CDK kinase activity in vitro and DNA replication in Xenopus egg extracts. A Cy motif is found near the N terminus of Cdc25A that is separate from the catalytic domain (Saha et al., 1997). Mutations in this motif disrupt the association of Cdc25A with cyclin E- or cyclin A-CDK2 in vitro and in vivo and selectively interfere with the dephosphorylation of cyclin E-CDK2. A peptide based on the Cy motif of p21 competitively disrupts the association of Cdc25A with cyclin-CDKs and inhibits dephosphorylation of the kinase. p21 inhibits Cdc25A-cyclin-CDK2 association and dephosphorylation of CDK2. Conversely, Cdc25A associates with cyclin-CDK and protects it from inhibition by p21. Cdc25A also protects DNA replication in Xenopus egg extracts from inhibition by p21. Thus, cdc25A and p21 compete for binding with cyclin-CDK complexes. The association of cdc25A, p21, cyclins and CDKs is mediated, in part, by the Cy motif The Cy motif sequence is found in many proteins involved in cell cycle dynamics (See Table 1).

TABLE 1

Sequences of Cy motif in Cell Cycle Related Proteins

| Protein with Cy motif | Motif Amino Acid Sequence | |
| --- | --- | --- |
| E2F1 | KRRLDL | (SEQ ID NO: 3) |
| E2F2 | KRKLDL | (SEQ ID NO: 4) |
| E2F3 | KRRLEL | (SEQ ID NO: 5) |
| P107Rb | KRRLFG | (SEQ ID NO: 6) |
| P130Rb | KRRLFV | (SEQ ID NO: 7) |
| Cdc6 | GRRLVF | (SEQ ID NO: 8) |

TABLE 1-continued

Sequences of Cy motif in Cell Cycle Related Proteins

| Protein with Cy motif | Motif Amino Acid Sequence | |
| --- | --- | --- |
| Myt1 | PRNLLS | (SEQ ID NO: 9) |
| Cdc25a | RRRLLF | (SEQ ID NO: 10) |
| P57 | CRSLFG | (SEQ ID NO: 11) |
| P27 | CRNLFG | (SEQ ID NO: 12) |
| P21(N) | NCRRLFG | (SEQ ID NO: 13) |
| P21(C) | KRRLIF | (SEQ ID NO: 14) |

In one embodiment of the invention multimeric repeats of Cy motifs controlled by an inducible system are used to provide multiple Cy inhibitory species in order to target CDK-cyclin activity. These Cy peptides are unlikely to be targeted by the 26 S proteosome, and thus afford a more stable means of triggering cell cycle inhibition and pseudo-senescence.

Antisense oligonucleotides also may be used to cause pseudo-senescence in a cell. Antisense methods have been used to block the cell cycle promoting activity of cyclins. Five stably transfected cell lines carrying a cyclin D1 antisense construct exhibited marked decrease of cell growth, in contrast to the original lines (A549 and NCI-H441) (Driscoll et al., 1997). The expression of several cell cycle-regulating proteins, including cyclin A, the cyclin-dependent kinases (CDK) 2 and CDK4, in addition to cyclin D1 itself, were also markedly decreased. The expression of one CDK inhibitor, p21 WAF1/CIP 1, was increased in the A549-derived cell lines that were stably transfected with antisense cyclin D (Driscoll et al., 1997). A specific target of cyclin D1 activity, the growth-suppressing product of the retinoblastoma gene, pRb exhibited decreased expression and a decreased level of phosphorylation in transfected cells. Decreased levels of pRb, due to a significant increase in its turnover rate, suggested that the stability of the protein may depend on phosphorylation by cyclin D1-dependent CDK activity. In addition to the impact on pRb stability, decreased expression of cyclin D1 induced susceptibility to cell death after withdrawal of exogenous growth factors in the cell lines transfected with antisense constructs, a response that was not observed in the original cancer cell lines. Apparently, abrogation of cyclin D1 overexpression in cancer cells disrupts several key pathways that are required for uncontrolled cell growth and induces those that lead to cell death after growth factor deprivation (Driscoll et al., 1997).

Conversely, using antisense oligonucleotides to block the actions of p27 leads to abrogation of quiescence (Rivard et al., 1996), while antisense inhibition of p21 prevents EGF-mediated cell cycle arrest (Ohtsubo et al., 1998).

One embodiment of this invention is to utilize antisense inhibitors of CDKs controlled by the inducible system to target CDK-cyclin activity via its activation rather than inhibition mechanism. Antisense technology can circumvent the processes of degradation of CKIs by the 26 S proteosome, and augments the RP shift via an alternative way of blocking the cell cycle and pseudo-senescence.

The present invention may also be used with yeast cells. Cellular and molecular studies of cyclins in invertebrate and vertebrate embryos have been preceded by genetic studies, particularly in ascomycete yeasts. In the fission yeast, the cdc13 gene encodes a B-type cyclin that acts in cooperation with cdc2 to regulate entry into mitosis (Booher & Beach, 1987; Booher & Beach, 1988; Booher et al., 1989; Dunphy et al., 1988; Gautier et al., 1988; Hagan et al., 1988; Solomon et al., 1988).

Genetic studies in both the budding yeast and fission yeast have revealed that cdc2 (or CDC28 in budding yeast) acts at two independent points in the cell cycle: mitosis and the so-called cell cycle "start" (Hartwell, 1971; Nurse & Bissett, 1981; Piggott et al., 1982; Reed & Wittenberg, 1990).

In budding yeast, the start function of the CDC28 protein requires association of the catalytic subunit of the protein kinase with ancillary proteins that are structurally related to A and B-type cyclins. This third class of cyclin has been called the CLN class, and three genes comprising a partially redundant gene family have been described (Hadwiger et al., 1989; Nash et al., 1988; Richardson et al., 1989). The CLN genes are essential for execution of start and in their absence, cells become arrested in the G I phase of the cell cycle. The CLN1 and CLN2 transcripts oscillate in abundance through the cell cycle, but the CLN3 transcript does not. In addition, the CLN2 protein has been shown to oscillate in parallel with its mRNA (Cross & Smith, 1988; Nash et al., 1988; Richardson et al., 1989; Wittenberg et al., 1990).

Although the precise biochemical properties conferred on cdc2/CDC28 by association with different cyclins have not been fully elaborated, genetic studies of cyclin mutants clearly indicate that they confer "G1" and "G2" properties on the catalytic subunit (Booher & Beach, 1987; Nash et al., 1988; Richardson et al., 1989).

The genes that control the cell cycle are evolutionarily conserved (Nurse, 1990). Complementation of mutations in yeast cdc2 with human CDKs reactivated cell cycle control (Lee & Nurse, 1987). CKIs that inhibit yeast CDKs have been documented (Mendenhall, 1993; Schwob et al., 1994) Since human CDKs are functional in yeast, the human CKIs may work as efficiently as the endogenous yeast forms. Therefore, the RP Shift vector containing human CKIs may be utilized in yeast. Blocking of cell division is to be assessed by measurements of cell number. Alternatively to the human CKIs, the endogenous yeast CKIs can be cloned into the RP shift vector.

The present invention also may be used with filamentous fungi. Most of the filamentous fungi important in biotechnology are members of the Deuteromycetes, including the *Aspergillus, Penicillium*, and *Trichoderma*. Basidiomycetes are also important in bioremediation. *Aspergillus* produces a number of secreted enzymes useful in the production of citric and gluconic acids that are both used as food additives. *Aspergillus* species express cyclins and CDKs with similar function to those found in yeast and human cells (Bussink & Osmani, 1998; Ye et al., 1999). The RP shift system expressing human CKIs or Cy motifs may be used in filamentous fungi.

Furthermore, the present invention may be used with bacterial cells. Bacterial cell division follows a cell cycle pattern as well (Bramhill, 1997). Bacteria usually divide by building a central septum across the middle of the cell. Apparently, the tubulin-like FtsZ protein plays a central role in cytokinesis as a major component of a contractile cytoskeleton. Assembly of FtsZ is a key point for regulation. The characterization of FtsZ homologues in Mycoplasmas, Archaea, and chloroplasts implies that the constriction mechanism is conserved, and that FtsZ can constrict in the absence of peptidoglycan synthesis (Bramhill, 1997). In most Eubacteria, the internal cytoskeleton must also regulate synthesis of septal peptidoglycan. The *E. coli* septum-specific penicillin-binding protein 3 (PBP3) forms a complex with other enzymes involved in murein metabolism, suggesting a centrally located transmembrane complex capable of splicing multiple new strands of peptidoglycan into the cell wall (Bramhill, 1997).

The cell cycle of *E. coli* does not have checkpoints, and several cycles may overlap (Donachie, 1993). It is the absence of such a checkpoint that results in the long filaments when division is blocked by mutation. *E coli* cells divide when they achieve a certain cellular volume. Expression of a gene encoding a cell division inhibitor from the sulA locus is activated as a part of the bacterial SOS response following DNA damage (Bi & Lutkenhaus, 1993; Sonezaki et al., 1995). Induction of the cell division inhibitor SulA, a component of the SOS response, or the inhibitor MinCD, a component of the min system, blocks formation of the FtsZ ring and leads to filamentation. Reversal of SulA inhibition by blocking protein synthesis in SuIA-induced filaments leads to a resumption of FtsZ ring formation and division (Bi & Lutkenhaus, 1993; Sonezaki et al., 1995). These results suggest that these inhibitors block cell division by preventing FtsZ localization into the central septum. In addition, analysis of min mutants demonstrated that FtsZ ring formation was also associated with minicell formation, indicating that all septation events in *E coli* involved the FtsZ ring (Bi & Lutkenhaus, 1993). It is an embodiment of this invention that cloning active cell division inhibitors SulA and MinC into a bacterial compatible RP shift vector will afford a means of blocking the cell cycle in *E. coli*.

Expression Vectors

The present invention provides expression vectors allowing tight transcriptional regulation of an encoded polypeptide. Such vectors are useful in methods of causing pseudosenescence in a cell transfected, transformed, or infected with the vector.

In certain embodiments, cells are produced or maintained that contain one or more expression vectors encoding one or more proteins that contribute to the induction of a pseudosenescent state in the cells. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques that are known to the skilled artisan.

Expression vectors may contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 micronx plasmid origin is suitable for yeast, and various viral origins (SV40, polyoma, adenovirus, VSV or BPV) are useful for cloning vectors in mammalian cells. However, in mammalian systems, it is preferred that the vector integrate into the genome thereby becoming dependent on the host for replication. Thus, in preferred embodiments, the vector is a retrovirus-based vector.

Expression vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells comprising the expression vector, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression vectors usually contain a promoter operably linked to the polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the polypeptide encoding region.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription in higher eukaryotes may be increased by inserting an enhancer or repressor sequence into the vector. Enhancers and repressors are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

In a preferred embodiment, an expression vector of the present invention contains a senescence-responsive element to increase the production of a recombinant protein. Additional amplification of the desired recombinant protein is achieved by engineering a senescence-responsive element into the vector upstream of a CMV promoter. A senescence-responsive element has been defined at the −89 to −66 sequence (5'-AGGATGTTATAAAGCATGAGTCA-3' (SEQ ID NO:2)) of the human collagenase gene (Campisi & Testori, 1999). Triggering the senescence phenotype by expression of the CKIs activates senescence-specific transcription factors, thereby accelerating transcription of the recombinant protein of interest. In certain embodiments, the senescence-responsive element may be operably connected to a bicistronic construct comprising a combination of desired recombinant product and the IRES-driven cell cycle inhibitors separately or both transcribed from the regulated promoter. Such a dicistronic design provides simultaneous regulated expression of the target protein and the cell cycle regulator.

In certain embodiments, an expression vector of the present invention contains elements that allow tight regulation of gene expression. For example, the expression vector may contain one or more tetracycline repressor binding sites (tetracycline operators) in the promoter region of the vector. In a preferred embodiment, the vector comprises multiple tetracycline operators and a minimal promoter comprising a TATA sequence. Preferably, the tetracycline operators are arranged to provide tight regulation of the promoter. One such arrangement includes two phased tetracycline operators 21 basepairs downstream from the TATA sequence and two phased tetracycline operators 11 basepairs upstream from the TATA sequence.

When vectors comprising tetracycline repressor binding regions are used, it is necessary to deliver the tetracycline repressor into the cells chosen for biopharmaceutical production. The tetracycline repressor may be introduced into these producer cells via a retroviral transduction using IRES-containing single-transcript vector (Levenson et al., 1998). After these producer cells are modified to express tetracycline repressor, the tetracycline-regulated construct containing the CKI is integrated into the genome of the producer cells by retroviral infection. Cells harboring the RP shift vector as stable transductants may be selected by resistance to the antibiotic G418. The expression of the delivered CKI or other cell-cycle inhibitor may then be induced by adding doxycycline (a stable derivative of tetracycline) into the media.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5" and, occasionally 3", untranslated regions of eukaryotic or viral DNAs or cDNAs. These regions contain nucleotide segments transcribed as polyadenylated fragments in the untranslated portion of the mRNA encoding the polypeptide.

Bioreactors

An important benefit of the present invention is the increase in protein yield from a cell culture. Many biotechnology products comprise a polypeptide isolated from a cell culture. Thus, many methods of isolating a desired protein from a cell culture are known in the art. The methods and compositions of the present invention may be utilized in conjunction with any of these methods to increase the yield of the protein.

Bioreactors are essentially any device or means for culturing cells. Bioreactors and methods of isolating proteins therefrom are well known in the art. Examples of bioreactors and their methods of use are described in U.S. Pat. Nos. 6,214,221; 6,100,061; 5,998,184; and 5,571,720. Bioreactors of the present invention include those that are stop-flow and flow-through.

EXAMPLES

The following examples are intended to illustrate the present invention without limitation.

Example 1

Figure 2:
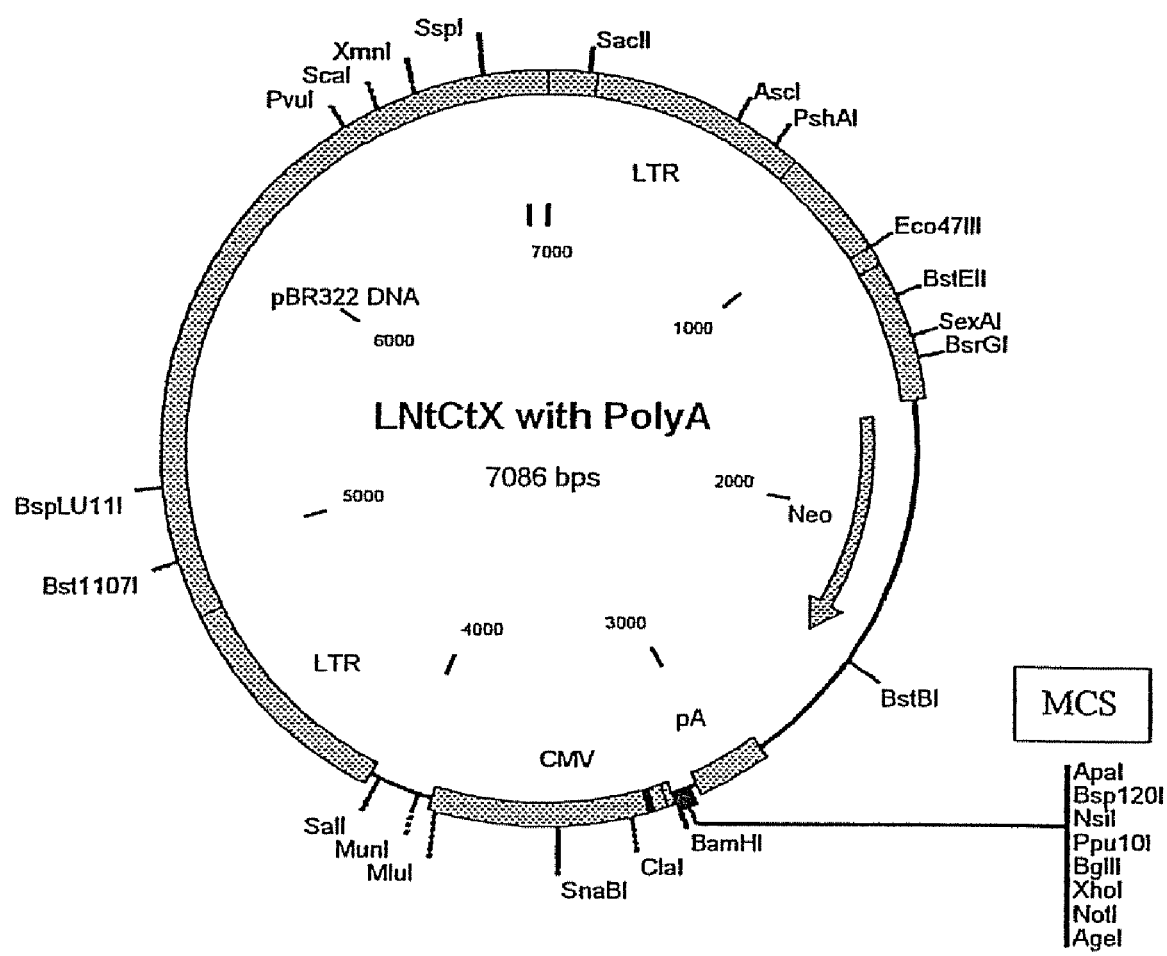
FIG. 2. is a map of the LNtCtX with PolyA vector.

This example describes the construction of a tetracycline-regulated retroviral vector (LNtCtX with PolyA). This expression vector can be (1) tightly regulated, to allow robust cell growth when in the OFF position; (2) is highly inducible by inexpensive and FDA-approved ligand; (3) is very promiscuous to allow efficient incorporation and subsequent expression in a wide variety of cells. The LNtCtX with PolyA vector was built from the mouse leukemia retroviral vector LNCX (W. S. Pear, G. P. Nolan, M. L. Scott, D. Baltimore, *Proc Natl Acad Sci USA* 90, 8392-6 (1993) with several important modifications. Its final form contains the viral long terminal repeat (LTR), a selection marker, and a multiple cloning site flanked by a polyadenylation signal and a regulated promoter (see FIG. 1). The sequence of the vector is provided in Table 2. A Mo-MSV LTR is encoded by basepairs 145-795 and basepairs 4089-4793. The retroviral packaging sequence is encoded within basepairs 796-1132. The neomycin resistance gene is encoded within basepairs 1194-2450. The bovine growth hormone polyadenylation signal is encoded within basepairs 3074-2843. Basepairs 3217-3176 and 3282-3235 each contain two tetracycline operators. Basepairs 3889-3235 encode a CMV promoter. Whereas basepairs 4794-7086 encode pBR322 DNA. A diagram of the LNtCtX with PolyA vector is provided by FIG. 2.

TABLE 2

Sequence of the RP shift vector (SEQ ID NO:1)

| | | | | | |
|---|---|---|---|---|---|
| gaattcatac | cagatcaccg | aaaactgtcc | tccaaatgtg | tcccctcac | 50 |
| actcccaaat | tcgcgggctt | ctgcctctta | gaccactcta | ccctattccc | 100 |
| cacactcacc | ggagccaaag | ccgcggccct | tccgtttctt | tgcttttgaa | 150 |
| agaccccacc | cgtaggLggc | aagctagctt | aagtaacgcc | actttgcaag | 200 |
| gcatggaaaa | atacataact | gagaatagaa | aagttcagat | caaggtcagg | 250 |
| aacaaagaaa | cagctgaata | ccaaacagga | tatctgtggt | aagcggttcc | 300 |
| tgccccggct | cagggccaag | aacagatgag | acagctgagt | gatgggccaa | 350 |
| acaggatatc | tgtggtaagc | agttcctgcc | ccggctcggg | gccaagaaca | 400 |
| gatggtcccc | agatgcggtc | cagccctcag | cagtttctag | tgaatcatca | 450 |
| gatgtttcca | gggtgcccca | aggacctaa | aatgaccctg | taccttattt | 500 |
| gaactaacca | atcagttcgc | ttctcgcttc | tgttcgcgcg | cttccgctct | 550 |
| ccgagctcaa | taaaagagcc | cacaacccct | cactcggcgc | gccagtcttc | 600 |
| cgatagactg | cgtcgcccgg | gtacccgtat | tcccaataaa | gcctcttgct | 650 |
| gtttgcatcc | gaatcgtggt | ctcgctgttc | cttgggaggg | tctcctctga | 700 |
| gtgattgact | acccacgacg | ggggtctttc | atttggggc | tcgtccggga | 750 |
| tttggagacc | cctgcccagg | gaccaccgac | ccaccaccgg | gaggtaagct | 800 |
| ggccagcaac | ttatctgtgt | ctgtccgatt | gtctagtgtc | tatgtttgat | 850 |
| gttatgcgcc | tgcgtctgta | ctagttagct | aactagctct | gtatctggcg | 900 |
| gacccgtggt | ggaactgacg | agttctgaac | acccggccgc | aaccctggga | 950 |
| gacgtcccag | ggactttggg | ggccgttttt | gtggcccgac | ctgaggaagg | 1000 |
| gagtcgatgt | ggaatccgac | cccgtcagga | tatgtggttc | tggtaggaga | 1050 |
| cgagaaccta | aaacagttcc | cgcctccgtc | tgaattttg | ctttcggttt | 1100 |
| ggaaccgaag | ccgcgcgtct | tgtctgctgc | agcgctgcag | catcgttctg | 1150 |
| tgttgtctct | gtctgactgt | gtttctgtat | ttgtctgaaa | attagggcca | 1200 |
| gactgttacc | actcccttaa | gtttgacctt | aggtcactgg | aaagatgtcg | 1250 |
| agcggatcgc | tcacaaccag | tcggtagatg | tcaagaagag | acgttgggtt | 1300 |

TABLE 2-continued

Sequence of the RP shift vector (SEQ ID NO:1)

```
accttctgct ctgcagaatg gccaaccttt aacgtcggat ggccgcgaga   1350
cggcaccttt aaccgagacc tcatcaccca ggttaagatc aaggtctttt   1400
cacctggccc gcatggacac ccagaccagg tcccctacat cgtgacctgg   1450
gaagccttgg cttttgaccc ccctccctgg gtcaagccct ttgtacaccc   1500
taagcctccg cctcctcttc ctccatccgc cccgtctctc cccttgaac    1550 ctcctcgttc gaccccgcct cgatcctccc tttatccagc cctcactcct   1600
tctctaggcg ccggaattcc gatctgatca agagacagga tgaggatcgt   1650
ttcgcatgat tgaacaagat ggattgcacg caggttctcc ggccgcttgg   1700
gtggagaggc tattcggcta tgactgggca caacagacaa tcggctgctc   1750
tgatgccgcc gtgttccggc tgtcagcgca ggggcgcccg gttcttttg    1800 tcaagaccga cctgtccggt gccctgaatg aactgcagga cgaggcagcg   1850
cggctatcgt ggctggccac gacgggcgtt ccttgcgcag ctgtgctcga   1900
cgttgtcact gaagcgggaa gggactggct gctattgggc gaagtgccgg   1950
ggcaggatct cctgtcatct caccttgctc ctgccgagaa agtatccatc   2000
atggctgatg caatgcggcg gctgcatacg cttgatccgg ctacctgccc   2050
attcgaccac caagcgaaac atcgcatcga gcgagcacgt actcggatgg   2100
aagccggtct tgtcgatcag gatgatctgg acgaagagca tcaggggctc   2150
gcgccagccg aactgttcgc caggctcaag gcgcgcatgc ccgacggcga   2200
ggatctcgtc gtgacccatg gcgatgcctg cttgccgaat atcatggtgg   2250
aaaatggccg cttttctgga ttcatcgact gtggccggct gggtgtggcg   2300
gaccgctatc aggacatagc gttggctacc cgtgatattg ctgaagagct   2350
tggcggcgaa tgggctgacc gcttcctcgt gctttacggt atcgccgctc   2400
ccgattcgca gcgcatcgcc ttctatcgcc ttcttgacga gttcttctga   2450
gcgggactct ggggttcgaa atgaccgacc aagcgacgcc caacctgcca   2500
tcacgagatt tcgattccac cgccgccttc tatgaaaggt tgggcttcgg   2550
aatcgttttc cgggacgccg gctggatgat cctccagcgc ggggatctca   2600
tgctggagtt cttcgcccac cccgggctcg atccctcgc gagttggttc    2650 agctgctgcc tgaggctgga cgacctcgcg gagttctacc ggcagtgcaa   2700
atccgtcggc atccaggaaa ccagcagcgg ctatccgcgc atccatgccc   2750
ccgaactgca ggagtgggga ggcacgatgg ccgctttggt cgaggcggat   2800
ctgctggttc tttccgcctc agaagccata gagcccaccg catccccagc   2850
atgcctgcta ttgtcttccc aatcctcccc cttgctgtcc tgccccaccc   2900
caccccccag aatagaatga cacctactca gacaatgcga tgcaatttcc   2950
tcattttatt aggaaaggac agtgggagtg caccttcca gggtcaagga    3000 aggcacgggg gaggggcaaa caacagatgg ctggcaacta aaggcacag    3050 tcgaggctga tcagcgagct ctagcattta ggtgacacta taagataggg   3100
ccctctagat gcataagctt agatctcgag cggccgcacc ggtccggatc   3150
cgagctcggt accaagctta agtttcctct ctatcactga tagggaaatc   3200
tctatcactg ataggagtc ttatatatct actagctccg gatcactatc     3250
```

TABLE 2-continued

| Sequence of the RP shift vector (SEQ ID NO:1) | |
|---|---|
| actgataggg aaatctctat cactgatagg gactagcatc gatagacctc | 3300 |
| ccaccgtaca cgcctaccgc ccatttgcgt caatggggcg gagttgttac | 3350 |
| gacattttgg aaagtcccgt tgattttggt gccaaaacaa actcccattg | 3400 |
| acgtcaatgg ggtggagact tggaaatccc cgtgagtcaa accgctatcc | 3450 |
| acgcccattg atgtactgcc aaaaccgcat caccatggta atagcgatga | 3500 |
| ctaatacgta gatgtactgc caagtaggaa agtcccataa ggtcatgtac | 3550 |
| tgggcataat gccaggcggg ccatttaccg tcattgacgt caataggggg | 3600 |
| cgtacttggc atatgataca cttgatgtac tgccaagtgg gcagtttacc | 3650 |
| gtaaatagtc cacccattga cgtcaatgga aagtccctat tggcgttact | 3700 |
| atgggaacat acgtcattat tgacgtcaat gggcggggt cgttgggcgg | 3750 |
| tcagccaggc gggccattta ccgtaagtta tgtaacgcgg aactccatat | 3800 |
| atgggctatg aactaatgac cccgtaattg attactatta ataactagtc | 3850 |
| aataatcaat gtcaacgcgt atatctggcc cgtacatcgc gaagcagcgc | 3900 |
| aaaacgccta accctaagca gattcttcat gcaattgtcg gtcaagcctt | 3950 |
| gccttgttgt agcttaaatt ttgctcgcgc actactcagc gacctccaac | 4000 |
| acacaagcag ggagcagata ctggcttaac tatgcggcat cagagcagat | 4050 |
| tgtactgaga gtcgaccata ggggatcggg agatccggcg ataaaataaa | 4100 |
| agattttatt tagtctccag aaaaagggg gaatgaaaga ccccacctgt | 4150 |
| aggtttggca agctagctta agtaacgcca ttttgcaagg catggaaaaa | 4200 |
| tacataactg agaatagaga agttcagatc aaggtcagga acagatggaa | 4250 |
| cagctgaata tgggccaaac aggatatctg tggtaagcag ttcctgcccc | 4300 |
| ggctcagggc caagaacaga tggaacagct gaatatgggc caaacaggat | 4350 |
| atctgtggta agcagttcct gccccggctc agggccaaga acagatggtc | 4400 |
| cccagatgcg gtccagccct cagcagtttc tagagaacca tcagatgttt | 4450 |
| ccagggtgcc ccaaggacct gaaatgaccc tgtgccttat ttgaactaac | 4500 |
| caatcagttc gcttctcgct tctgttcgcg cgcttctgct ccccgagctc | 4550 |
| aataaaagag cccacaaccc ctcactcggg gcgccagtcc tccgattgac | 4600 |
| tgagtcgccc gggtacccgt gtatccaata aaccctcttg cagttgcatc | 4650 |
| cgacttgtgg tctcgctgtt ccttgggagg gtctcctctg agtgattgac | 4700 |
| tacccgtcag cggggtctt tcatttgggg gctcgtccgg gatcgggaga | 4750 |
| ccccctgccca gggaccaccg acccaccacc gggaggtaag ctggctgcct | 4800 |
| cgcgcgtttc ggtgatgacg gtgaaaacct ctgacacatg cagctcccgg | 4850 |
| agacggtcac agcttgtctg taagcggatg ccgggagcag acaagcccgt | 4900 |
| cagggcgcgt cagcgggtgt tggcgggtgt cggggcgcag ccatgaccca | 4950 |
| gtcacgtagc gatagcggag tgtatactgg cttaactatg cggcatcaga | 5000 |
| gcagattgta ctgagagtgc accatatgcg gtgtgaaata ccgcacagat | 5050 |
| gcgtaaggag aaaataccgc atcaggcgct cttccgcttc ctcgctcact | 5100 |
| gactcgctgc gctcggtcgt tcggctgcgg cgagcggtat cagctcactc | 5150 |
| aaaggcggta atacggttat ccacagaatc agggataac gcaggaaaga | 5200 |

TABLE 2-continued

Sequence of the RP shift vector (SEQ ID NO:1)

```
acatgtgagc aaaaggccag caaaaggcca ggaaccgtaa aaaggccgcg   5250
ttgctggcgt ttttccatag gctccgcccc cctgacgagc atcacaaaaa   5300
tcgacgctca agtcagaggt ggcgaaaccc gacaggacta taaagatacc   5350
aggcgtttcc ccctggaagc tccctcgtgc gctctcctgt tccgaccctg   5400
ccgcttaccg gatacctgtc cgcctttctc ccttcgggaa gcgtggcgct   5450
ttctcatagc tcacgctgta ggtatctcag ttcggtgtag gtcgttcgct   5500
ccaagctggg ctgtgtgcac gaaccccccg ttcagcccga ccgctgcgcc   5550
ttatccggta actatcgtct tgagtccaac ccggtaagac acgacttatc   5600
gccactggca gcagccactg gtaacaggat tagcagagcg aggtatgtag   5650
gcggtgctac agagttcttg aagtggtggc ctaactacgg ctacactaga   5700
aggacagtat ttggtatctg cgctctgctg aagccagtta ccttcggaaa   5750
aagagttggt agctcttgat ccggcaaaca aaccaccgct ggtagcggtg   5800
gtttttttgt ttgcaagcag cagattacgc gcagaaaaaa aggatctcaa   5850
gaagatcctt tgatctttc tacggggtct gacgctcagt ggaacgaaaa   5900
ctcacgttaa gggattttgg tcatgagatt atcaaaaagg atcttcacct   5950
agatcctttt aaattaaaaa tgaagtttta atcaatcta aagtatatat    6000
gagtaaactt ggtctgacag ttaccaatgc ttaatcagtg aggcacctat   6050
ctcagcgatc tgtctatttc gttcatccat agttgcctga ctccccgtcg   6100
tgtagataac tacgatacgg gagggcttac catctggccc cagtgctgca   6150
atgataccgc gagacccacg ctcaccggct ccagatttat cagcaataaa   6200
ccagccagcc ggaagggccg agcgcagaag tggtcctgca actttatccg   6250
cctccatcca gtctattaat tgttgccggg aagctagagt aagtagttcg   6300
ccagttaata gtttgcgcaa cgttgttgcc attgctgcag gcatcgtggt   6350
gtcacgctcg tcgtttggta tggcttcatt cagctccggt tcccaacgat   6400
caaggcgagt tacatgatcc cccatgttgt gcaaaaaagc ggttagctcc   6450
ttcggtcctc cgatcgttgt cagaagtaag ttggccgcag tgttatcact   6500
catggttatg gcagcactgc ataattctct tactgtcatg ccatccgtaa   6550
gatgcttttc tgtgactggt gagtactcaa ccaagtcatt ctgagaatag   6600
tgtatgcggc gaccgagttg ctcttgcccg gcgtcaacac gggataatac   6650
cgcgccacat agcagaactt taaaagtgct catcattgga aaacgttctt   6700
cggggcgaaa actctcaagg atcttaccgc tgttgagatc cagttcgatg   6750
taacccactc gtgcacccaa ctgatcttca gcatctttta ctttcaccag   6800
cgtttctggg tgagcaaaaa caggaaggca aaatgccgca aaaaagggaa   6850
taagggcgac acggaaatgt tgaatactca tactcttcct ttttcaatat   6900
tattgaagca tttatcaggg ttattgtctc atgagcggat acatatttga   6950
atgtatttag aaaaataaac aaataggggt tccgcgcaca tttccccgaa   7000
aagtgccacc tgacgtctaa gaaaccatta ttatcatgac attaacctat   7050
aaaaatagge gtatcacgag gccctttcgt cttcaa                  7086
```

The Moloney strain murine leukemia virus vector LNCX contains a regulated promoter and polyadenylation site are positioned in reverse orientation to the LTR to prevent read-through from the LTR, thereby eliminating LTR-initiated expression leakage. At the same time, reverse orientation of polyadenylation signal does not interfere with genomic RNA transcription in packaging cells.

LNCX was modified according to Kistner to contain an array of seven cognate tetracycline operator sequences linked to a minimal CMV promoter which is itself inactive (A. Kistner, et al., *Proc Natl Acad Sci USA* 93, 10933-8. (1996). This arrangement was additionally modified in the LNtCtX with PolyA by the insertion of two phased tetracycline operators 21 bp downstream from the TATA site and two phased tetracycline operators 11 bp upstream of the TATA sequence within the CMV promoter. This configuration positions a tight protein clamp of two dimerized TetR elements both in front of the TF-IID contact site and also exactly at the site of initiation of transcription. Moreover, binding of dimerized tetracycline repressors induces a significant kink in the double helix, further reducing the probability of fortuitous transcription.

cDNAs for the CKIs p16, p21, p27, and p57, in sense orientation, are individually cloned into the multiple cloning site (MCS) to be expressed from the regulated promoter. These vectors are referred to herein as RP shift vectors.

Example 2

This example describes the production of infectious viral particles using a expression vector of the present invention and the subsequent infection of target cells. This delivery system employs a pantropic system to deliver the DNA to the cells. VSV-G, an envelope glycoprotein, is used to mediate viral entry into cells through lipid binding and plasma membrane fusion (J. C. Burns, T. Friedmann, W. Driever, M. Burrascano, J. K. Yee, *Proc Natl Acad Sci USA* 90, 8033-7 (1993); J. K. Yee, et al., *Proc Natl Acad Sci USA* 91, 9564-8 (1994); and N. Emi, T. Friedmann, J. K. Yee, *J Virol* 65, 1202-7 (1991)). Because this system does not depend on specific cell surface receptors, the pantropic system allows transduction of any mitotically active cells. Infectious pantropic retroviral particles carrying the gene of interest were transfected into GP2-293 cells using standard Ca-phosphate (W. S. Pear, G. P. Nolan, M. L. Scott, D. Baltimore, *Proc Natl Acad Sci USA* 90, 8392-6 (1993) technique. Twenty-four hours after transfection culture medium with infectious virions was collected, filtered through 0.45 μm filter to remove stray packaging cells, supplemented with Polybrene™ (4 μg/ml) and added to the target cells. Twenty-four hours later cells were trypsinized and re-plated: two 60-mm plates will be seeded with 200 cells each, while the rest of the cells is plated into 150-mm plates at a density of $10^6$ cells per plate. All cells in 150-mm plates and one of the 60-mm plates were selected with G418 (0.7 mg/ml for 10 days) to eliminate uninfected cells. The second 60-mm plate is left without antibiotic. An infection rate of 55% was determined by colony formation by dividing the number of colonies in G418-treated 60-mm plate by the number of colonies in its untreated companion.

Since retroviral rearrangements are expected in 10-15% of infected cells (V. V. Levenson, E. D. Transue, I. B. Roninson, *Hum Gene Ther* 9, 1233-6 (1998) it was desirable to isolate 10-20 individual colonies from the infected and G418-selected 150-mm plate.

Target cell lines must be able to encounter and receive viral particles produced by packaging cell lines. In the case of human cells, VSV-G viral coat proteins are used so that fusion of the viral particles to plasma membrane affords infection of target cells. In the case of hybridoma cells, which are formed by fusing human myeloma cells with mouse splenocytes so that they express ecotropic receptor, mouse derived retroviral vectors may be used.

Example 3

In this Example, the present invention is used to increase the production of the secreted enzyme plasminogen activator inhibitor type 1 (PAI-1). HT1080 E-14 cells actively produce PAI-1 (S. H. Kang, et al., *Int J Cancer* 77, 620-5 (1998)). HT1080 E-14 cells expressing tetracycline repressor with a nuclear localization signal (A. Kistner, et al., *Proc Natl Acad Sci USA* 93, 10933-8. (1996)) were prepared via a retroviral transduction using an IRES-containing single-transcript vector (V. V. Levenson, E. D. Transue, I. B. Roninson, *Hum Gene Ther* 9, 1233-6 (1998)). After these producer cells were modified to express tetracycline repressor, a tetracycline-regulated RP shift construct containing a CKI (p16) was integrated into the genome of the producer cells by retroviral infection. Cells harboring the RP shift vector as stable transductants were selected by resistance to the antibiotic G418.

The CKI was inducted by addition of 2 μM doxycyclin. Cell proliferation, as monitored by uptake of methylene blue dye, was immediately blocked. Cells exposed to doxycyclin develop a large, flattened appearance associated with the senescence phenotype (Campisi, 2000). Furthermore, the onset of pseudo-senescence was observed by staining cells for senescence associated-β-galactosidase (G. P. Dimri, et al., *Proc Natl Acad Sci USA* 92, 9363-7 (1995)).

Figure 3:
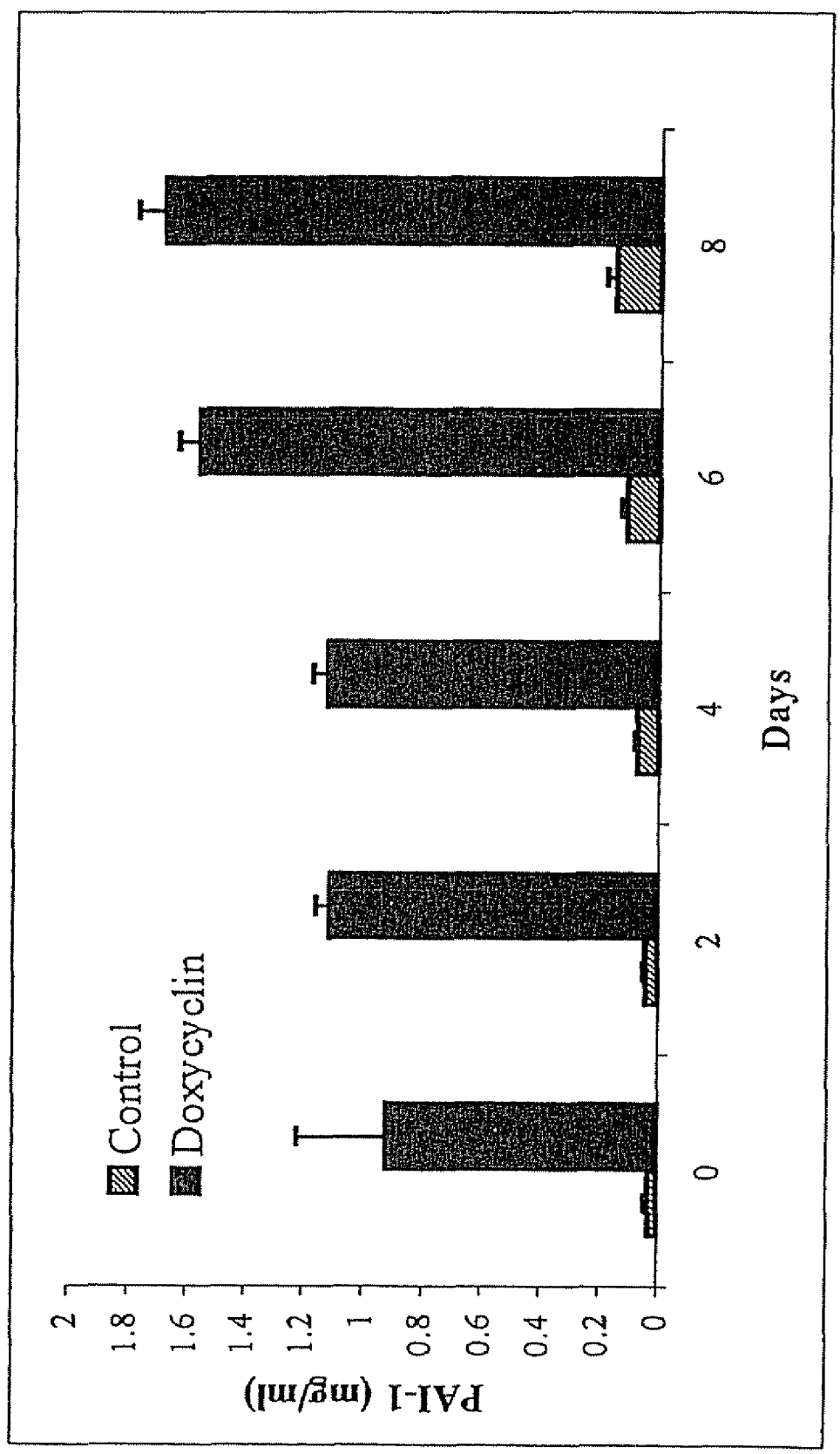
FIG. 3. shows enhanced production of secreted enzyme from cells blocked by RP Shift.

The amount of plasminogen activator inhibitor-1, a protein normally secreted by HIT1080 cells, was monitored by ELISA assays using anti-PAI-1 alkaline phosphatase conjugate (S. M. Wileman, et al., *Br J Ophthalmol* 84, 417-22 (2000)). As FIG. 3 indicates, secreted protein levels were increased by as much as 30-fold.

Example 4

This example demonstrates that the present invention is useful for increasing the production of monoclonal antibodies from hybridoma cell lines. Since hybridoma cells contain ecotropic receptor, they should be infected by RP Shift retrovirus without use of VSV-G. To demonstrate the infectability of hybridoma cells, Enhanced Green Fluorescent Protein (Clontech Laboratories) was cloned into the RP Shift vector. This retroviral vector (10 μg) was transfected into $5 \times 10^6$ BOSC packaging cells and media containing viral particles was added to 500,000 hybridoma cells twice over 48 h. The percent infected cells enhanced green fluorescent protein was monitored by flow cytometry 48 h after addition of 2 μM doxycyclin.

The expression of CKIs p21, p57, and p16 in these cells were also assessed by RT-PCR. Cells harboring CKI constructs were selected using appropriate G418 (1 mg/ml) for the resistance genes engineered into the retroviral construct. Expression of the CKIs prevents cell cycle progression and induces a pseudo-senescent state blocking further cell division and expanding the protein synthesis capacity of the cells. The effects of RP Shift on cell cycle progression in hybridoma cells was assessed by monitoring DNA content of the cells. S-phase, the segment of the cell cycle when DNA is duplicated, was suppressed in cells undergoing RP Shift. This result indicates that the hybridoma cells had stopped dividing.

Cells in the pseudo-senescent state were tested for resistance to apoptosis by assessing cell viability and cell number after 3 weeks in culture. Cell number varied little over this time period, indicating that the cells are stable in long term culture.

The production of monoclonal antibody was monitored by ELISA using anti-IgG alkaline phosphatase conjugate. The population of hybridoma cells undergoing RP Shift increased production of monoclonal antibody by nearly 8-fold after one week in culture. These examples demonstrate that RP Shift can be used to block cell division of mammalian cells and a concomitant enhanced production of native protein from these cells.

What is claimed is:

1. A eukaryotic cell comprising an inducible transcription regulator element, said inducible transcription regulator element further comprising: a minimal promoter comprising a TATA sequence and at least two sets of paired tetracycline operator elements, wherein the tetracycline operator elements are arranged wherein a first set comprising a first and a second phased tetracycline operator are downstream from the TATA sequence, and a second set comprising a third and a fourth phased tetracycline operator are upstream from the TATA sequence.

2. The cell of claim 1, wherein the first set of two phased tetracycline operators downstream from the TATA sequence begin at a position 21 basepairs downstream from the position of the TATA sequence in the expression vector.

3. The cell of claim 1, wherein the second set of two phased tetracycline operators upstream from the TATA sequence begin at a position 11 basepairs upstream from the position of the TATA sequence in the expression vector.

4. The cell of claim 1, wherein: (a) the first set of two phased tetracycline operators downstream from the TATA sequence begin at a position 21 basepairs downstream from the position of the TATA sequence in the expression vector; and (b) the second set of two phased tetracycline operators upstream from the TATA sequence begin at a position 11 basepairs upstream from the position of the TATA sequence in the expression vector.

5. The cell of claim 1, wherein the minimal promoter is a CMV promoter.

6. The cell of claim 1, further comprising a viral vector.

7. The cell of claim 6, wherein the viral vector is a retroviral vector.

8. The cell of claim 7, wherein the retroviral vector is a Moloney strain murine leukemia virus vector.

9. The cell of claim 1, further comprising a gene operably linked to the promoter.

10. The cell of claim 1 further comprising one or a plurality of cyclin dependent kinase inhibitor genes operably linked to the promoter.

11. The cell of claim 10, wherein the cyclin dependent kinase inhibitor is selected from the group consisting of p21, p27, p57, p15, p16, p18, and p19.

12. The cell of claim 11, wherein the vector encodes more than one cyclin-dependent kinase inhibitor selected from the group consisting of p21, p27, p57, p15, p16, p18, and p19.

13. A eukaryotic cell comprising an inducible recombinant expression construct encoding a cyclin dependent kinase inhibitor gene.

14. The cell of claim 13, wherein the inducible recombinant expression construct comprises a nucleic acid encoding one or a plurality of Cy motifs.

15. The cell of claim 14, wherein the Cy motif is selected from the group consisting of E2F1 (SEQ ID NO: 3), E2F2 (SEQ ID NO: 4), E2F3 (SEQ ID NO: 5), P107Rb (SEQ ID NO: 6), P130Rb (SEQ ID NO: 7), Cdc6 (SEQ ID NO: 8), Myt1 (SEQ ID NO: 9), Cdc25a (SEQ ID NO: 10), P57 (SEQ ID NO: 11), P27 (SEQ ID NO: 12), P21(N) (SEQ ID NO: 13), and P21(C) (SEQ ID NO: 14).

16. The cell of claim 15, wherein the Cy motif inhibits CDK-cyclin activity.

17. The cell of claim 1 further comprising one or a plurality of cyclin antisense constructs operably linked to the promoter.

18. The cell of claim 17, wherein the cyclin antisense construct is a D1 antisense construct.

19. The cell of claim 18, wherein the D1 antisense construct inhibits CDK-cyclin activity.

* * * * *

UNITED STATES PATENT AND TRADEMARK OFFICE
CERTIFICATE OF CORRECTION

| | | |
|---|---|---|
| PATENT NO. | : 7,851,219 B2 | Page 1 of 1 |
| APPLICATION NO. | : 12/136317 | |
| DATED | : December 14, 2010 | |
| INVENTOR(S) | : Todd Bucciarelli et al. | |

It is certified that error appears in the above-identified patent and that said Letters Patent is hereby corrected as shown below:

Title Page; item (54);
1. The title of the issued patent:

"Methods and Compositions for Increasing Protein Yield from a Cell Culture"
is incorrect, and should be replaced with:
"Eukaryotic Cells with Increased Protein Yield and Methods of Use Thereof".

Col. 39, line 18;

2. In claim 13, first line, of the issued patent, the phrase:
"A eukaryotic cell"
is incorrect, and should be replaced with:
"The eukaryotic cell of claim 1".

Signed and Sealed this
Twenty-second Day of February, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,851,219 B2 | Page 1 of 1 |
| APPLICATION NO. | : 12/136317 | |
| DATED | : December 14, 2010 | |
| INVENTOR(S) | : Todd Bucciarelli et al. | |

It is certified that error appears in the above-identified patent and that said Letters Patent is hereby corrected as shown below:

Title Page; item (54) and at Column 1, lines 1-3;
1. The title of the issued patent:

"Methods and Compositions for Increasing Protein Yield from a Cell Culture"
is incorrect, and should be replaced with:
"Eukaryotic Cells with Increased Protein Yield and Methods of Use Thereof".

Col. 39, line 18;

2. In claim 13, first line, of the issued patent, the phrase:
"A eukaryotic cell"
is incorrect, and should be replaced with:
"The eukaryotic cell of claim 1".

This certificate supersedes the Certificate of Correction issued February 22, 2011.

Signed and Sealed this
Twenty-second Day of March, 2011

David J. Kappos
*Director of the United States Patent and Trademark Office*